United States Patent [19]
Takatsu et al.

[11] Patent Number: 5,916,767
[45] Date of Patent: Jun. 29, 1999

[54] DNA ENCODING HUMAN INTERLEUKIN-5 RECEPTOR

[75] Inventors: Kiyoshi Takatsu, 301-32, Ishiharamachi, Kumamoto-shi, Kumamoto-ken; Akira Tominaga; Satoshi Takagi, both of Kumamoto; Yoshiyuki Murata, Shimonoseki, all of Japan

[73] Assignee: Kiyoshi Takatsu, Japan

[21] Appl. No.: 08/939,727

[22] Filed: Oct. 3, 1997

Related U.S. Application Data

[62] Division of application No. 08/442,282, May 16, 1995, Pat. No. 5,760,204, which is a division of application No. 07/757,390, Sep. 10, 1991, Pat. No. 5,453,491.

[30] Foreign Application Priority Data

Sep. 11, 1990 [JP] Japan ................................ 2-240638

[51] Int. Cl.$^6$ ............................ C12N 15/09; C12N 15/00
[52] U.S. Cl. ................. 435/69.1; 435/252.3; 435/320.1; 536/23.5
[58] Field of Search ................... 536/23.5; 435/69.1, 435/252.3, 320.1

[56] References Cited

U.S. PATENT DOCUMENTS

| | | | |
|---|---|---|---|
| 4,859,609 | 8/1989 | Dull et al. | 436/501 |
| 5,006,459 | 4/1991 | Kung et al. | 435/5 |

FOREIGN PATENT DOCUMENTS

| | | |
|---|---|---|
| 8428720 | 7/1989 | Australia . |
| A-0 325 474 | 7/1989 | European Pat. Off. . |
| A-0 367 566 | 5/1990 | European Pat. Off. . |
| 0 492 214 A2 | 1/1992 | European Pat. Off. . |
| WO-A-9 007 518 | 7/1990 | WIPO . |

OTHER PUBLICATIONS

Gearing et al *EMBO* 8, 1989, 3667–76.
Hayashida et al, *PNAS* 87, 1990, pp. 9655–9659.
Garman et al *PNAS* 87, 1990, pp. 5459–5463.
Bozon, Immunol. Today 11(10):350–354 (1990).
Cosman, DNA and Protein Engineering Techniques 2(1):1–3 (1990).
Devas et al., Biochem. Biophys. Res. Comm. 172(2):570–75 (1990).
Devas et al., EMBO 10(8):2133–37 (1991).
Dover et al., J. Clin. Immunol. 10(6):289–99 (1990).
Gearing et al., EMBO Journal 8:3667–3676 (1989).
Guvernier et al., PNAS 89:7041–45 (1992).
Hitoshi et al., J. Immunol. 144:4218–4225 (1990).
Hitoshi, et al., 1989, "Interferon–gamma inhibits the proliferation but not the differentiation of murine B cells in response to IL–5", Int. Immunol., 1(2):185–90.
Hitoshi et al., 1990, "Distribution of IL–5 receptor–positive B cells", J. of Immunol., 144:4218–25.
Kaczmerski et al., Blood Res. 5(3):193–203 (1991).
Kinashi et al., 1986, "Cloning of complementary DNA encoding T–cell replacing factor and identify with B–cell growth factor II", Nature, 324(6092):70–73.
Matsumoto et al., 1989, Interleukin–5 induces maturation but not class switching of surface Iga–positive B cells into IgA–secreting cells, Immunology, 66:32–38.
Migita et al., 1991, "Characterization of the human IL–5 receptors on eosinophils", Cell. Immunol., 133:484–97.
Mita al., PNAS 86:2311–15 (1989).
Mita et al., 1988, "Receptors for T cell–replacing factor/ interleukin 5", J. Exp. Med., 168:863–78.
Mita et al., 1989, "Rapid methods for purification of human recombinant interleukin–5 (IL–5) using the anti–murine IL–5 antibody–coupled immunoaffinity column", J. Immunol. Methods, 125:233–41.
Mita et al., 1989, "Characterization of high–affinity receptors for interleukin 5 on interleukin 5–dependent cell lines", Proc. Natl. Acad. Sci. USA 86:2311–15.
Murata et al., 1990, "Interleukin 5 and interleukin 3 induce serine and tyrosine phosphorylations of several cellular proteins in an interleukin 5–dependent cell line", Biochem. and Biophys. Res. Comm., 173(3):1102–08.
Rolink et al., J. Exp. Med. 169:1693–1701 (1989).
Sanderson et al., 1988, "Molecular and cellular biology of eosinophil differentiation factor (interleukin–5) and its effects on human and mouse B cells", Immunological Reviews, 102:29–50.
Sonoda et al., 1989, "Transforming growth factor β induces Iga production and acts additively with interleukin 5 for IgA production", J. Exp. Med., 170:1415–20.
Spry, Christopher J.F., 1988, Eosinophils: a comprehensive review, and guide to the scientific and medical literature, Oxford University Press, 262–287.
Takaki et al., EMBO Journal 9:4367–4374 (1990).
Takaki et al., Lymphokine Research 9:572 (1990).
Takaki et al., 1990, "Molecular cloning and expression of the murine interleukin–5 receptor", EMBO Journal, 9(13):4367–74.
Takaki et al., 1991, Identification of the second subunit of the murine interleukin–5 receptor: interleukin–3 receptor– like protein, AIC2B is a component of the high affinity interleukin–5 receptor, *The EMBO Journal* 10(10):2833–2838.

(List continued on next page.)

*Primary Examiner*—Garnette D. Draper
*Attorney, Agent, or Firm*—Pennie & Edmonds LLP

[57] ABSTRACT

The invention provides an isolated cDNA sequence coding for murine interleukin 5 receptor, murine secretory interleukin 5 receptor, human interleukin 5 receptor, and human secretory interleukin 5 receptor and products including murine interleukin 5 receptor, murine secretory interleukin 5 receptor, and human interleukin 5 receptor which are produced using the isolated cDNA sequence. These products may be useful for a therapeutic agent for autoimmune disorders and diseases with eosinophilia in which human IL-5 is believed to be involved.

10 Claims, 10 Drawing Sheets

OTHER PUBLICATIONS

Takatsu et al., 1988, "T cell–replacing factor (TRF)/interleukin 5 (IL–5): molecular and functional properties", Immunological Reviews, 102:107–135.

Takatsu and Tominaga, 1990, "Interleukin 5 as a hematopoietic cell growth and differentiation factor", Growth Factors, Differentiation Factors, and Cytokines, A. Habenicht (ed.), 147–62.

Tavernier et al., Cell 66:1175–1184 (1991).

Tominaga et al., 1988, "Molecular properties and regulation of mRNA expression for murine T cell–replacing factor/IL–5", J. Immunol., 140(4):1175–81.

Tominaga et al., 1989, "Establishment of IL–5–dependent early B cell lines by long–term bone marrow cultures", Growth Factors, 1:135–46.

Tominaga et al., 1990, "Role of carbohydrate of moiety of IL–5", J. Immunol., 144(4):1345–52.

Yamaguchi et al., 1989, "Mechanisms of the interleukin 5–induced differentiation of B cells", 106(5):837–843.

Yamaguchi et al., International Immuno. 2:181–88 (1990).

Yamaguchi et al., 1990, "Characterization of the murine interleukin 4 receptor by using a monoclonal antibody", Int. Immunol., 2(2):181–87.

DNA ENCODING HUMAN INTERLEUKIN-5 RECEPTOR

This application is a divisional of application Ser. No. 08/442,282, filed May 16, 1995 now U.S. Pat. No. 5,760,204 currently allowed, which in turn is a divisional of application Ser. No. 07/757,390, filed Sep. 10, 1991, now issued U.S. Pat. No. 5,453,491.

BACKGROUND OF THE INVENTION

1. Field of the Invention

The present invention relates to isolated cDNA sequences coding for murine interleukin 5 receptors, murine secretory interleukin 5 receptors and human interleukin 5 recepeors and to murine interleukin 5 receptors, murine secretory interleukin 5 receptors and human interleukin 5 receptors which are produced using the isolated cDNA sequences as well as to methods of producing the interleukin 5 receptors.

2. Prior Art

Interleukin 5 (referred to as "IL-5", hereinafter) is a proliferation and differentiation factor for eosinophils and B lineage cells (Immunol. Rev. 102: 29, 107.,1988). It has been known that IL-5 is produced especially by T cells primed with *Mycobacterium tuberculosis*, parasites or allo-antigens (J. Immunol. 140: 1175, 1988; Nature, 324: 70, 1986). IL-5 has also been known to induce production of IgM class immunoglobulin including anti-DNA antibody. Recently, IL-5 has been suspected of involvement in autoimmune diseases and there is a report that IL-5 is closely associated with eosinophilia accompanied by autoantibody production, fascitis and myositis(Eosinophils, Oxford University Press, 1988).

There are two types of IL-5 receptors (referred to as "IL-5R", hereinafter), namely, membrane bound IL-5R and secretory IL-5R. Among them, mouse secretory IL-5R is able to bind to human IL-5 and therefore expected to serve as a therapeutic agent for diseases associated with IL-5.

The inventors have obtained IL-5 responsive early B cells, T 88 and T-88M by culturing mouse bone marrow cells in the presence of IL-5 (Growth Factors 1: 135 1989) and produced IL-5R. The cross-linking reaction and subsequent SDS-PAGE analysis have revealed that IL-5R comprises at least two types of subunits, one having a molecular weight of about 46,500 and the other having a molecular weight of about 114,000, and that there are two types of IL-5R, a low affinity IL-5R having the dissociation constant of 27 nM and a high affinity IL-5R having the dissociation constant of 150 pM. It has been believed that the low affinity IL-5R comprises the small subunit of an estimated molecular weight of 46,500 while a high affinity IL-5R comprises the large subunit (MW: 114,000) and the small subunit (46,500) (Proc. Natl. Acad. Sci. USA 86: 2311, 1989).

The inventors have produced H7 and T21 monoclonal antibodies by immunizing rats with a membrane fraction of T88-M cells, which inhibit the binding of IL-5 to IL-5R (Int. Immunol. 2: 181, 1990; J. Immunol. 144: 4218, 1990). Anti-IL-5R antibodies, H7 and T21, are found to bind to glycoprotein of the molecular weight of about 60,000 according to the SDS-PAGE analysis. The real molecular weight of the small subunit is found to be about 55,000 according to the binding assay using IL-5 free of an oligosaccharide, suggesting that the low affinity IL-5R comprises a single molecule of molecular weight of about 60,000 (Int. Immunol. 2: 181, 1990).

We have also reported recently that IL-5R is found on the cell surface of human eosinophils. The dissociation constant of human IL-5R is 170–330 pM and the molecular weight is 55,000–60,000 according to the SDS-PAGE analysis. Human IL-5R appears to be comparable to a low affinity murine IL-5R (Migita, M., Yamaguchi, N., Mita, S:, Higuchi, S., Hitoshi, Y., Yoshida, Y., Tomonaga, M., Matsuda, I., Tominaga, A., Takatsu, K., 1991, Cellular Immunology, 133: 484–497).

There has been no report on the isolation of a DNA sequence coding for the low affinity murine/human IL-5R. An object of the invention is to isolate the DNA sequence coding for the low affinity murine/human IL-5R and to determine the DNA sequence. The isolated DNA sequence may be used to produce murine/human IL-5R in mammalian cells. Another object of the invention is to obtain a DNA sequence coding for secretory IL-5R which is distinct from the DNA sequence coding for membrane bound IL-5R and to produce pure secretory IL-5R using the DNA.

The present irivention is characterized by the following description:

(1). An isolated cDNA sequence coding for murine interleukin 5 receptor which is synthesized from murine early B cell mRNA.

(2). The isolated cDNA sequence of (1) wherein the nucleotide sequence comprises the open reading frame sequence described in SEQ ID No.1.

(3) The isolated cDNA sequence of (1) wherein the nucleotide sequence comprises the entire sequence described in SEQ ID No.2.

(4). An isolated cDNA sequence coding for secretory murine IL-5R which is synthesized from murine early B cell mRNA.

(5) The isolated cDNA sequence of (4) wherein the nucleotide sequence comprises the open reading frame sequence described in SEQ ID No.3.

(6). The isolated cDNA sequence of (4) wherein the nucleotide sequence comprises the entire sequence described in SEQ ID NO.4.

(7). An isolated murine interleukin 5 receptor wherein the amino acid sequence comprises the sequence described in SEQ ID No.5.

(8). An isolated murine interleukin 5 receptor wherein the amino acid sequence comprises the sequence described in SEQ ID No.6.

(9) An isolated murine secretory interleukin 5 receptor wherein the amino acid sequence comprises the sequence described in SEQ ID No.7.

(10) An isolated murine secretory interleukin 5 receptor wherein the amino acid sequence comprises the sequence described in SEQ ID No.8.

(11). A method of producing the murine interleukin 5 receptors which comprises culturing cells capable of expressing the murine interleukin 5 receptors in medium and isolating the murine interleukin 5 receptors from the cells or the culture supernatant using anti-interleukin 5 receptor antibodies.

(12) A COS 7 monkey cell (ATCC CRL1651) transfected with a recombinant vector containing the cDNA sequence of any one of (1)–(6).

(13) A method of producing the murine interleukin 5 receptors and the murine secretory interleukin 5 receptors comprises culturing the COS 7 cell transfected with relevant DNA in medium, and recovering the murine interleukin 5 receptors from the cells or secretory murine interleukin 5 receptors from the culture supernatant.

(14). An isolated cDNA sequence coding for human interleukin 5 receptor which is synthesized from mRNA of a human peripheral blood eosinophil.

(15). The isolated cDNA sequence of (14) wherein the nucleotide sequence described in SEQ ID No. 9 comprises the open reading frame sequence coding for human interleukin 5 receptor.

(16). The isolated cDNA sequence of (14) wherein the nucleotide sequence described in SEQ ID No.10 comprises the entire sequence coding for human interleukin 5 receptor.

(17). The isolated cDNA sequence of (14) wherein the nucleotide sequence described in SEQ ID No. 11 comprises the open reading frame sequence coding for human interleukin 5 receptor 2.

(18). The isolated cDNA sequence of (14) wherein the nucleotide sequence described in SEQ ID No. 12. comprises the entire sequence coding for human interleukin 5 receptor 2.

(19). An isolated human interleukin 5 receptor wherein the amino acid sequence comprises the sequence described in SEQ ID NO.13.

(20). An isolated human interleukin 5 receptor wherein the amino acid sequence comprises the sequence described in SEQ ID NO.14.

(21). The isolated cDNA sequence of (14) coding for a whole or part of amino acid residue numbers 1–333 described in SEQ ID No. 13.

(22). A secretory human interleukin 5 receptor which lacks a cytoplasmic region and a transmembrane region of human interleukin 5 receptor.

(23). An expression vector comprising the cDNA sequence of any one of (14), (15), (16), (17), (18), and (21).

(24). A method of producing the secretory human interleukin 5 receptor and its analogues which comprises culturing a recombinant vector coding for the secretory human interleukin 5 receptor under the conditions which promote the expression thereof and recovering the secretory human interleukin 5 receptor.

SUMMARY OF THE INVENTION

The invention provides isolated DNA sequences coding for murine/human IL-5R and pure murine IL-5R produced by a genetic engineering technique using the isolated DNA sequence as well as an isolated DNA sequence coding for secretory murine IL-5R. The DNA sequence coding for secretory murine IL-5R is especially valuable in constructing a nucleotide sequence corresponding to the sequence of secretory human IL-5R and in producing secretory human IL-5R using the DNA sequence. The secretory human IL-5R thus produced may be utilized as a therapeutic agent for autoimmune disorders or diseases with eosinophilia in which IL-5 is believed to be involved and may greatly contribute to the medical and pharmaceutical field.

BRIEF DESCRIPTION OF THE DRAWINGS

The Invention is explained referring to the attached drawings.

DETAILED DESCRIPTION OF THE INVENTION

The description which relates to murine IL-5R is indicated (Murine) and which relates to human IL-5R is indicated (Human).

Preparation of Poly(A)$^+$ RNA from Mouse Bone Marrow Cells (Murine)

In order to prepare the cDNA coding for the IL-5R, mRNAs are recovered from the mouse bone marrow cells having IL-5R. Mouse bone marrow cells are obtainable by a long-term bone marrow cell culture in the presence of IL-5 (Growth Factor 1: 135, 1989). A suitable source of cells may be a Balb/c mouse bone marrow long-term culture cell line, Y16, which is early B cells and shows a strong response to IL-5 (even at a concentration of 1 pg/ml of IL-5). RNA is prepared from the cell according to the method described by Okayama et al. (Methods in Enzymology 154: 3 1987). Poly(A)⁺ RNA is recovered by fractionating the total RNA with the affinity chromatography using an oligo (dT) cellulose column.

Construction of cDNA Library from mRNA (Murine)

Figure 2A:
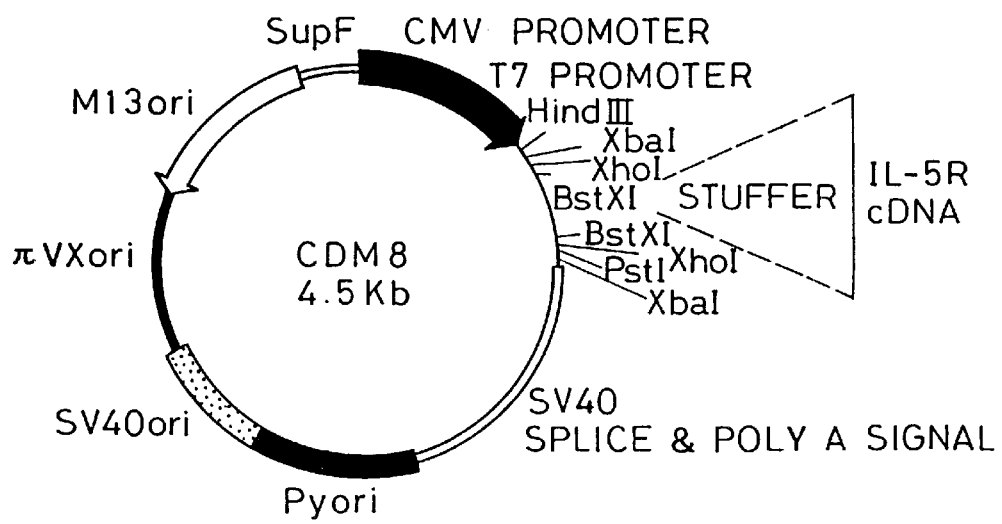
FIGS. 2A–2B shows vectors used in the present invention and a site of inserting an isolated DNA into the vector.

The poly(A)⁺ RNA is reverse transcribed to cDNA using random primers and reverse transcriptase (Gene 25: 263, 1983). The cDNA larger than 1.0 kb is selected for cloning and inserted into the BstXI site of CDM 8 vector (see FIG. 2A) containing a cytomegalovirus promoter according to the method described by Seed et al. (Proc. Natl. Acad. Sci. USA 84: 8573, 1987). E. coli is transformed with the recombinant plasmid in order to provide cDNA library expressible in mammals.

Cloning of IL-5R Gene: Transfection of COS7 Cells Using the DNA of the Transformant (Murine)

COS 7 cells (Green monkey kidney cells) are transfected with the DNA according to the DEAE dextran or protoplast fusion method. The COS7 transformant is screened using anti-IL-5R antibodies H7 and T21 according to the method described by Seed et al. (Nature 329: 840, 1988). H7 and T21 antibodies and the COS7 suspension are incubated together. After incubation, the mixture is transferred to plates coated with goat anti-rat IgG antibody (H7 and T21 are rat IgG antibodies). Then, plasmid DNA is recovered from the COS7 cells immobilized on the bottom of the plate. The transformation-screening procedure described above is repeated several times. After screening, a group of the selected COS7 transformant is further screened by flow cytometry using fluorescein-conjugated H7 and T21 and the transformant containing IL-5R cDNA is identified.

The Entire Structure of murine IL-5R Genes (Murine)

Figure 1:
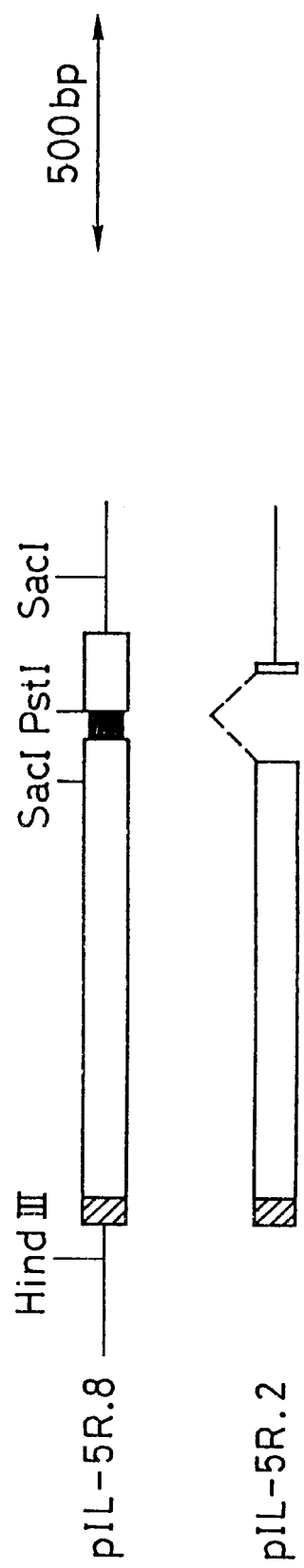
FIG. 1 shows partial restriction maps of two IL-5R cDNA clones. The box indicates an open reading frame which is expected to be translated. The shaded portion at the 5'-end indicates a signal peptide, and the solid portion indicates the transmembrane region.

The rough restriction maps of IL-5R cDNA isolated above are shown in FIG. 1. pIL-5R.8 is the cDNA clone prepared first from the CDM 8 library. pIL-5R.2 is obtained from the cDNA library using the HindIII-PstI fragment of pIL-5R.8 as a probe according to the colony hybridization method.

The nucleotide sequences of the cDNA fragments of pIL-5R.2 and pIL-5R.8 are determined according to the method described by Sanger et al (Proc. Natl. Acad. Sci. USA 74: 5463, 1977). The entire nucleotide sequence of the cDNA fragment of pIL-5R.8 and the deduced amino acid sequence are shown in SEQ ID No.15. The nucleotide A of the initiation codon ATG is numbered 1 and the amino acid methionine is numbered 1. The cDNA fragment of pIL-5R.8 has 1808 nucleotides in length which codes for 415 amino acids. This polypeptide consists of 4 portions according to Hydropathy plot (OF URFS and ORFS, Rusell F, Doolittle, University Science Books, 1987): singal peptide (See amino acids 1–17 SEQ ID No.15), extracellular region, transmembrane region, and cytoplasmic region. Amino acids 32–34, 128–130, 213–215, 241–243, 392–394 and 412–414 are presumably linked to N-linked oligosaccharide. pIL-5R.2 lacks a transmembrane region (FIG. 1 and SEQ ID No. 16) and therefore, IL-5R expressed by pIL-5R.2 is a secretory type. As shown in SEQ ID No.16, pIL-5R.2 lacks the sequence between the nucleotide Nos. 986 and 1164.

Expression of IL-5R gene (Murine)

Figure 2B:
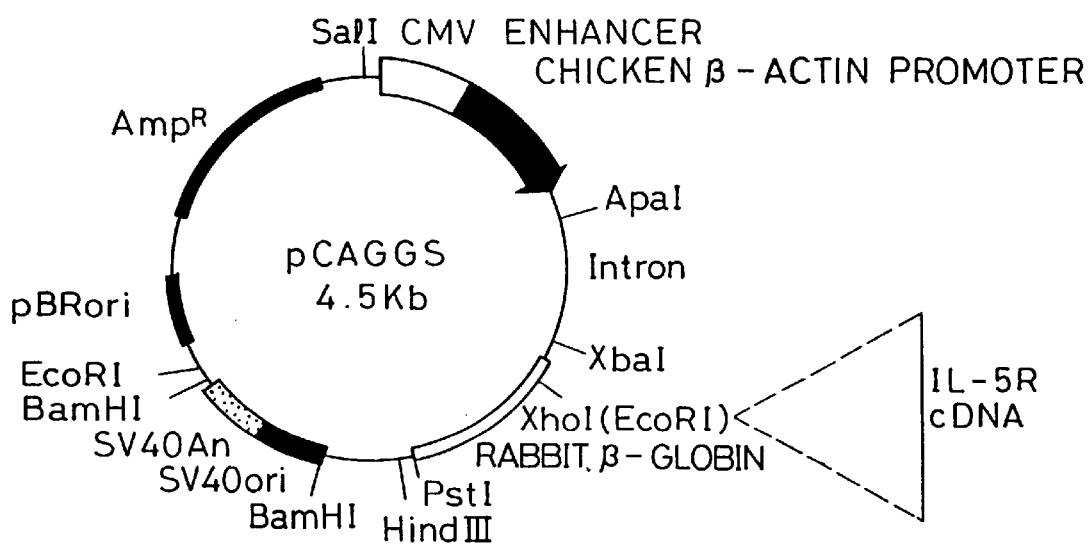

The following two types of vectors, CDM8 and pCAGGS, can be utilized as expression vectors for an isolated IL-5R cDNA sequence (see FIG. 2).

CDM 8 vector: The vector demonstrates an elevated DNA expression in mammalian cells. The vector has two BstXI sites. The vector is digested with BstXI and both ends of cDNA of interest are ligated to a BstXI linker. The cDNA-linker complex is ligated to the BstXI digested vector.

pCAGGS vector: The vector contains a CMV enhancer upstream of the promoter of pAGS-3, which is a vector having a much stronger expression ability than that of CDM8 (Gene, 79: 269, 1989). The cDNA insertion site of pCAGGS is XhoI site substituted with EcoRI site in the exon of rabit β-globin gene region. The PCAGGS vector demonstrate a higher level of DNA product expression than pAGS-3.

In the Example of the invention, the pCAGGS vector is used for expression test of IL-5R and the expressed murine IL-5R is tested by IL-5 binding test, IL-5 cross-linking test and immunoprecipitation test using monoclonal antibody, H7.

The murine IL-5R cDNA encoding a secretory IL-5R is inserted into the XhoI (EcoRI) site of the pCAGGS vector. COS7 (Green monkey kidney cell, ATCC CRL1651) is transfected with the recombinant plasmid and the resulting transformant is grown in a medium. The amino acid sequence of the peptide in the culture supernatant is determined. The N-terminal 20 amino acids thus determined are the same as those deduced from the nucleotide sequence of the murine IL-5R cDNA. The COS7 culture supernatant containing soluble IL-5R inhibits the binding of IL-5 to IL-5R expressed on B cells or eosinophils.

Binding Assay of IL-5R to IL-5 (Murine)

The COS7 transformant thus obtained is tested for the production of IL-5R capable of binding to IL-5 using $^{35}S$-methionine and $^{35}S$-cysteine labeled IL-5 (J. Immunol. 140: 1175, 1988; J. Exp. Med. 168: 863, 1988). Binding of the labeled IL-5 is inhibited by the excess amount (100-fold) of the non-labelled IL-5 and thus the cDNA clone pIL-5R.8 is confirmed to code for IL-5R.

Cross-linking of IL-5R to IL-5 and Immunoprecipitation of IL-5R to IL-5 (Murine)

COS7 cells are transfected with pIL-5R.8 followed by cross-linking reaction and immunoprecipitation.

Cross-linking: IL-5R produced by the transformant is tested whether it is the same as those expressed by a IL-5 responsive early B cell, T88-M, by the cross-linking test using $^{35}S$-labeled IL-5 (Proc. Natl. Acad. Sci. USA, 1989, 86: 2311). After electrophoresis, the band pattern on the gel indicates that the molecular weight comparable to IL-5 monomer is decreased (about 22,000) under reduced condition.

Immunoprecipitation: The surface proteins of the transfected cells is $^{125}I$-labeled and immunoprecipitated with anti-IL-5R antibodies, H7 (Int. Immunol. 2: 181, 1990). IL-5R produced by the transformant is found to have a molecular weight of 60,000.

Cell Lines Expressing IL-5R mRNA and the Size of the IL-5R mRNA (Murine)

Poly(A)⁺ RNA are prepared from IL-5 responsive cell lines such as Y16 (early-B cell), BCL1-B20 (mouse B cell chronic leukemia lymphoma, in vitro line), mouse myeloma cell, MOPC104E, X5568, L cell, IL-3 responsive cell line FDC-P1 derived from mouse bone marrow long-term cultured cell, and IL-2 responsive mouse T cell lines. 2 μg of each of poly(A)⁺ RNA are tested for the presence of IL-5R mRNA by Northern blot.

Northern blot is carried out using the HindIII-PstI fragment of pIL-5R.8 as a probe (Biochemistry 16: 4743, 1977). IL-5 responsive cell lines including Y16, BCL1-B20, MOPC104E are found to express IL-5R mRNA with the size of 5–5.8 kb Preparation of Poly(A)⁺ RNA from Human Peripheral Blood Eosinophils (Human)

A DNA sequence coding for human IL-5R is prepared from human peripheral blood eosinophils. Eosinophils are isolated from peripheral blood of healthy volunteers and of a patient with eosinophilia by a density gradient centrifugation using Ficoll (Migita, Y., et al. supra). Whole mRNA is prepared from eosinopbils according to the method described by Okayama et al. (ibid). Poly(A)+ RNA is recovered by fractionating the whole RNA with the affinity chromatography using an oligo (dT) cellulose column. One of the poly(A)+ RNA preparation is derived from healthy volunteers and the other is derived from a patient with eosinophilia.

Construction of cDNA Library from mRNA (Human)

The poly(A)+ RNA is reverse transcribed to cDNA using random primers and reverse transcriptase as described above. The cDNA of more than 1.0 kb fragments is selected for cloning. The cDNA fragment derived from eosinophils of healthy volunteers (helv-cDNA) is inserted into the BstXI site of vector pAGS-3 (Miyazaki, et al., 1989, Gene, 79: 269) according to the method described by Seed et al. (ibid). *E. coli* is then transformed with the recombinant plasmid (helv-cDNA library). The cDNA derived from eosinophils of patients with eosinophilia (eosi-cDNA) is inserted into the EcoRI site of phage λgt10 using an EcoRI linker. *E. coli* is then infected with the recombinant phage (eosi-cDNA library).

Screening of helv-cDNA and eosi-cDNA Libraries for Human IL-5R (Human)

The helv-cDNA library is screened using the HindIII-PstI fragment of pIL-5R.8. A positive clone is isolated and is designated as ph5R.1. ph5R.1 lacks some of the nucleotide sequence of IL-5R. Subsequently, the eosi-cDNA library is screened using the nucleotide sequence of ph5R.1. Two positive clones designated as HSIL5R and HSIL5R2 are isolated.

Human IL-5R Gene Structure (Human)

Figure 6:
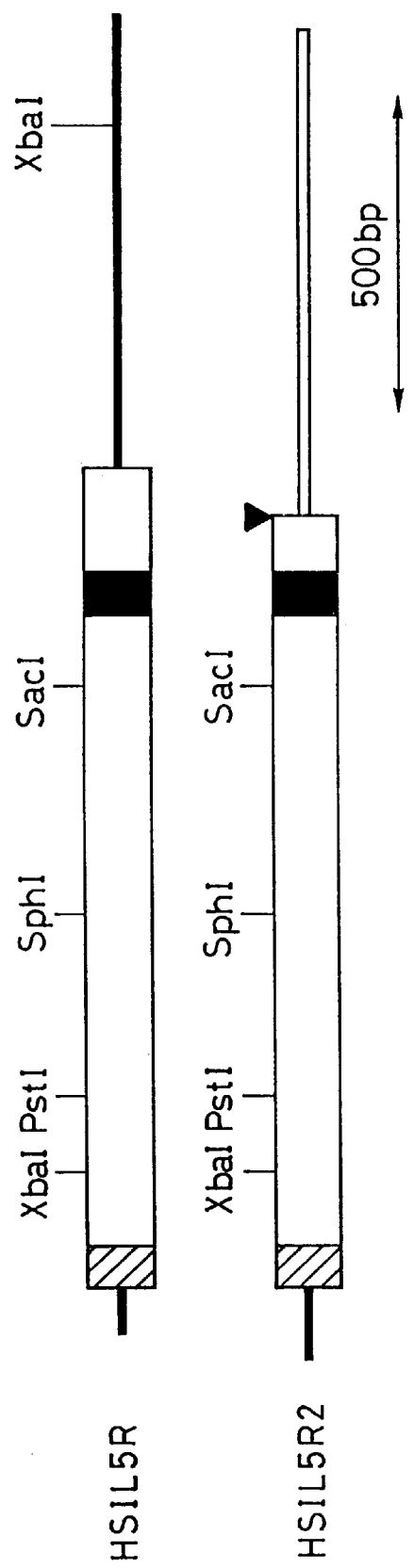
FIG. 6 shows a restriction map of a human IL-5R cDNA fragment of HSIL5R and HSIL5R2. The box represents the open reading frame of IL-5R. The 5' end hatched box is a putative signal peptide and the solid box is the predicted transmembrane region. The mark ▼ indicates the starting point of the nucleotide sequence which distinguishes HSIL5R from HSIL5R2.

FIG. 6 shows restriction maps of the isolated IL-5R cDNAs of HSIL5R and HSIL5R2. The nucleotide sequence was determined according to the Sanger's method (ibid). HSIL5R and HSIL5R2 are membrane bound receptors. The cytoplasmic domain sequence of HSIL5R2 is shorter than that of HSIL5R.

SEQ ID No.17 and No. 18 show the nucleotiode and deduced amino acid sequence of HSIL5R (420 amino acids in length) and HSIL5R2 (396 amino acid in length), respectively. The amino acid sequence is analyzed as described above.

HSIL5R and HSIL5R2 consist of signal peptide region, extracellular region, transmembrane region, cytoplasmic region. The nucleotide sequence downstream of the mark nucleotide 1184 distinguishs HSIL5R (SEQ ID No.17) from HSIL5R2 (SEQ ID No.18). The amino acid sequence of HSIL5R2 terminates after amino acid Ile (amino acid number 396).

Expression of Human IL-5R (Human)

Human IL-5R cDNA is inserted into a pCAGGS vector, and COS 7 cells are transfected with the recombinant plasmid. λgt10 cDNA clones, HSIL5R and HSIL5R2 are digested with EcoRI and the IL-5R cDNA fragment is inserted into the EcoRI site of pCAGGS.

Binding Assay of transfectants with HSIL5R or HSIL5R2 to IL-5 (Human)

The IL-5R expression of the clones are tested using $^{35}$S-methionine- and $^{35}$S-cysteine-labeled murine IL-5 or $^{125}$I-labeled human IL-5. The human IL-5 is prepared as follows:

The IL-5 cDNA fragment is inserted into an expression vector derived from baculovirus. *Sf*21 cells (*Spodotera frugiperda*) are infected with the recombinant DNA. The cell are cultured and the culture supernatant is tested for human IL-5 using anti-IL-5 monoclonal antibody, NC17 (Proc. Natl. Acad. Sci. U.S.A. 84: 4581, 1987). The isolated human IL-5 is labeled with $^{125}$I. Binding assay is carried out as described for murine IL-5R.

Cross-linking of IL-5R to IL-5 (Human)

IL-5R produced by the positive clones is tested whether it is the same as those produced by eosinophils, by cross-linking test using $^{35}$S-labeled murine IL-5 and $^{125}$I-labeled human IL-5 as described above.

Cell Lines Expressing IL-5R mRNA and the Size of the IL-5R mRNA (Human)

Poly(A)+ RNA may be prepared from human eosinophils, erythroleukemic cell line TF-1, eosinophilic leukemia cell line EoL-3, ATL-2 adult T cell leukemia cell line ATL-2, Burkitt's lymphoma cell line Raji, and histiocytic lymphoma cell line U-937. 6 μg of each of poly(A)+ RNA is tested for the presence of IL-5R mRNA using the entire sequence of HSIL5R cDNA as a probe. Human eosinophils and TF-1 cell line are found to express IL-5R mRNA with the size of 1.4 kb and 5.3 kb.

Production of Secretory Human IL-5R

HSIL5R cDNA is inserted into the EcoRI site of Bluescript SK(−). The construct is digested with SalI and KpnI. The SalI-KpnI digested fragment is then incubated with exonuclease III so that the sequence coding for the cytoplasmic domain and transmembrane domain of human IL-5R can be removed. The digested fragment is blunted with mung bean exonuclease followed by a treatment with a klenow fragment and subjected to ligation (Gene 33: 103, 1985). After treatment, a clone is obtained which contains deletion from 3' end to the nucleotide number 995 (SEQ ID No. 17), a site which corresponds to the starting point of deletion in the secretory murine IL-5R cDNA. The deletion mutant is digested with EcoRI and BssHII. The resulting DNA fragment is ligated to a linker containing a stop codon. After ligation, a DNA-linker complex is inserted into an appropriate restriction site of any vector. Alternatively, the HSIL-5R cDNA fragment of the Bluescript SK(−) construct is deleted from 3' end to the nucleotide number 996. As a result of frameshift, the construct contains two stop codons. The secretory human IL-5R construct thus obtained lacks DNA sequences for a cytoplasmic domain and a transmembrane domain and codes for 333 amino acids.

The secretory human IL-5R construct is introduced into host cells and the transfectant produces a secretory human IL-5R. An expression vector is selected according to host cells to be transfected. Host cells include prokaryotes such as gram negative bacteria (*E. coli*) or gram positive bacteria (Bacillus), yeast, and eukaryotic cell lines derived from insects and mammals.

EXAMPLES

The following Examples are described for murine secretory IL-5R and membrane type IL-5R.

Preparation of Polyadenylated RNA from Y16 Cell (Murine)

Y16 ($2\times10^7$) cells were placed in a 3 liter Spinner culture bottle containing a medium (RPMI 1640, 4% FCS, $5\times10^{-5}$M 2-mercaptoethanol, 100 U/ml of penicillin, 100 μg/ml of streptomycin) and 300 pg/ml of IL-5. The bottle was sealed and incubated for a week. After incubation, about $5\times10^9$ cells were harvested. $1\times10^9$ cells were solubilized in 50 ml of 5.5 M guanidium thiocyanate solution (pH7.0) containing 25 mM sodium citrate, 0.5% sodium laurylsulcosine, and 0.2M 2-mercaptoethanol according to the method described by Okayama et al. (supra). The cell lysate was layered onto cesium trifluoroacetic acid solution (density: 1.5 g/ml) containing 0.1M EDTA/pH7.0. The mixture was centrifuged at 15° C., at 125,000 g, for 24 hours. After centrifugation, the RNA pellet was dissolved in distilled water containing 10 mM Tris-HCl/pH7.5 and 1 mM EDTA. The RNA solution was loaded onto an oligo (dT) cellulose column and the pass-through was loaded onto the column again (Molecular Cloning, 1989, Chapter 7, p26, Cold Spring Harbor Laboratory Press). The oligo (dT) bounded fraction was eluted and 30 μg of poly(A)+ RNA was recovered.

Construction of cDNA Library in CDM8 (Murine)

30 μg of the poly(A)+ RNA thus obtained was used to synthesize cDNA using a cDNA synthesis kit (BRL, Bethesda, Md.) according to the method described by Seed (supra). The CDM8 vector (see FIG. 2A) was digested with BstXI. After digestion, an approximately 4100 bp fragment was purified by a potassium acetate density gradient centrifugation. The cDNA was ligated to a BstXI linker and a cDNA-linker complex containing cDNA having a size of 1,000 bp or more was selected by a potassium acetate density gradient centrifugation. The fractionated fragments were subjected to ligation with the purified CDM8 vector. $E.$ $coli$ MC1061/P3 was transformed with the construct and about 2 million transformants were obtained as a cDNA library.

Screening of the cDNA Library (Murine)

COS7 ($5 \times 10^5$) cells were placed in each of 100 plates (6 cm). The following day, the COS7 cell was transfected with 2 μg of the plasmid DNA (per plate) prepared from the cDNA library according to the DEAE-dextran method. On day 3, the COS7 cells were removed from the plates and incubated with antibodies, H7 and T21. The COS7 cell was screened for the presence of the H7 and T21 antigens using goat anti-rat IgG antibodies (Panning technique). After screening, plasmid DNAs were prepared from the H7 and T21 antigen positive COS7 cells. Then, $E.$ $coli$ MC1061/P3 was transformed with the plasmid DNAs. Fresh COS7 cells were fused with the transformants according to the protoplast fusion method. The COS7 cells were screened for the presence of the H7 and T21 antigens according to the Panning technique. After four cycles of the procedure described above, fresh COS7 cells were transformed and the transformant was screened by the Panning technique using goat anti-rat IgG antibody F(ab')$_2$ fragment. This transformation-screening procedure was repeated two times in order to eliminate the contamination of Fc receptor genes. After screening, 50 independent colonies were selected and the plasmid DNA was prepared. Fresh COS7 cells were then transfected with the plasmid DNA and the transformants were tested for the presence of the H7 and T21 antigens. One of the transformants was found to be antigen positive and designated as pIL-5R.8.

The cDNA library prepared from Y16 as described above was screened for the presence of IL-5R cDNA using the fragment inserted in pIL-5R.8 as a probe according to the colony hybridization method (Molecular Cloning, 1989, chapter 1, p90, Cold Spring Harbor Laboratory Press): The HindIII-PstI fragment was prepared from pIL-5R.8 and radiolabeled with α-$^{32}$P-dCTP according to the random primer method. The transformants of the cDNA library were grown on a solid LB agarose medium (approximately 10,000 colonies per 10 cm plate) overnight. The colonies were transferred to a nitrocellulose membrane and the DNAs on the membrane were hybridized to the radiolabeled prove. Positive colonies were identified through autoradiography. One of the transformants was isolated and designated as pIL-5R.2.

Nucleotide Sequencing of IL-5R (Murine)

The cDNA fragment of pIL-5R.8 was digested with XbaI and inserted into a M13mp19 vector. The construct was digested with BamHI and KpnI. The BamHI-KpnI digested fragment was then digested with exonuclease III: the fragment was digested up to ten minutes with stopping digestion every minute. The digested fragment was blunted with mungbean exonuclease followed by a treatment with a klenow fragment and subjected to ligation (Gene 33: 103, 1985). $E.$ $coli$ JM109 was transformed with the constructs to produce different sizes of the M13 deletion mutants. Single-stranded DNAs were prepared from the mutants (Methods in Enzymology 101: 58, 1983) and the nucleotide sequence was determined using the M13 primer, 5'-GTTTTCCCAGTCACGAC-3' according to the Sanger's method. Single-stranded DNA was also prepared from the M13 mutant containing the cDNA fragment of a reversed orientation and the nucleotide sequence was determined as described above. The nucleotide sequence thus obtained from the M13 mutant containing the cDNA fragment of a right orientation was found to be complementary to the one of M13 mutant containing the cDNA fragment of a reversed orientation.

SEQ ID No. 15 shows the complete nucleotide sequence of pIL-5R.8. The N-terminal 17 amino acids (1–17) are believed to be the signal peptide (Nucleic. Acids. Res. 14: 4683, 1986) and amino acids 340–361 are considered to be the transmembrane region according to the hydropathy plot. Amino acids 32–34, 128–130, 213–215, 241–243, 392–394 and 412–414 indicate that the region appears to be bounded to a N-linked oligosaccharide. The previously estimated molecular weight (45,284) of IL-5R differs from the real molecular weight (about 60,000) of IL-5R produced by the COS7 cells transfected with pIL-5.8. The difference of the weight may be due to the addition of N-linked oligosacharide. The deleted nucleotide sequence of pIL-5R.2 would be between nucleotides 1164 and 1165. The nucleotide sequence of pIL-5R.2 shown in SEQ ID No.16 was determined using primers(17-mers) synthesized based on the nucleotide sequence of pIL-5R.8, a T7 primer (5'-ATGGAAATTAATACG-3'), and a primer for the 3' end of CDM8 (5'-TGCAGGCGCAGAACTGG-3') according to the Sanger's method. The pIL-5R.2 is a frame shift mutant, resulting in translation termination to give 4 peptides. The polypeptide encoded by pIL-5R.2 is a secretory IL-5R which is likely to act on B cells or eosinophils in the process of differentiation.

Expression and Binding Test of IL-5R cDNA (Murine)

pIL-5R.8 (CDM8 vector) was digested with XhoI and the IL-5R cDNA fragment was inserted into the XhoI site of pCAGGS vector (see FIG. 2B) whose EcoRI site had been replaced with a XhoI site.

The new construct was designated as pCAGGS.5R. 8. $E.$ $coli$ was transformed with the construct and the transformant was designated as $E.$ $coli$ 5R.8. $E.$ $coli$ 5R.8 was deposited with Fermentation Research Institute, Agency of Industrial Science and Technology and was assigned the accession number FERM BP 3085.

COS7 cells were transfected with pIL-5R.8 or pCAGGS.5R.8 and the cells were harvested two days later. $2-10 \times 10^4$ cells were incubated with different concentrations of $^{35}$S-labeled IL-5 ($2.5 \times 10^8$ cpm/μg) in the presence or absence of 100-fold excess of non-labeled IL-5 at 37° C. for 10 minutes. After incubation, the number of IL-5 binding per cell was counted and the dissociation constant was calculated.

Figure 3A:
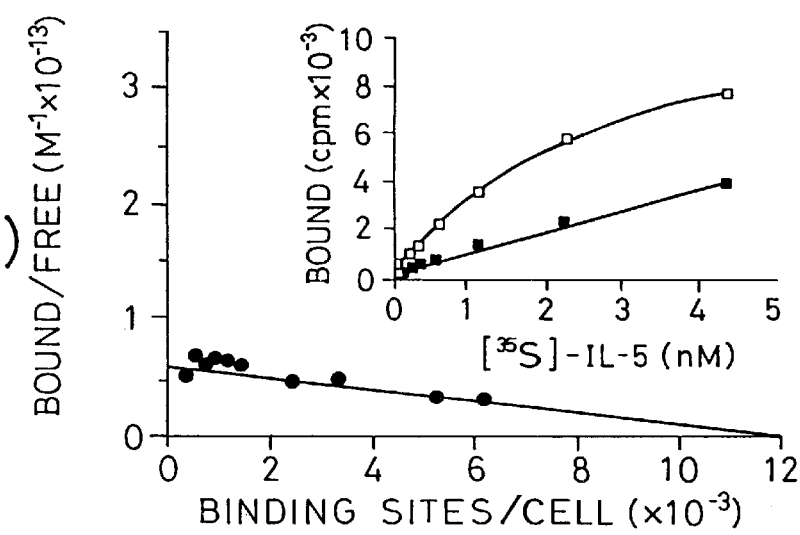
FIGS. 3A–3C shows the results of binding assay using $^{35}$S-labeled IL-5 and the Scatchard plot analysis.
Figure 3B:
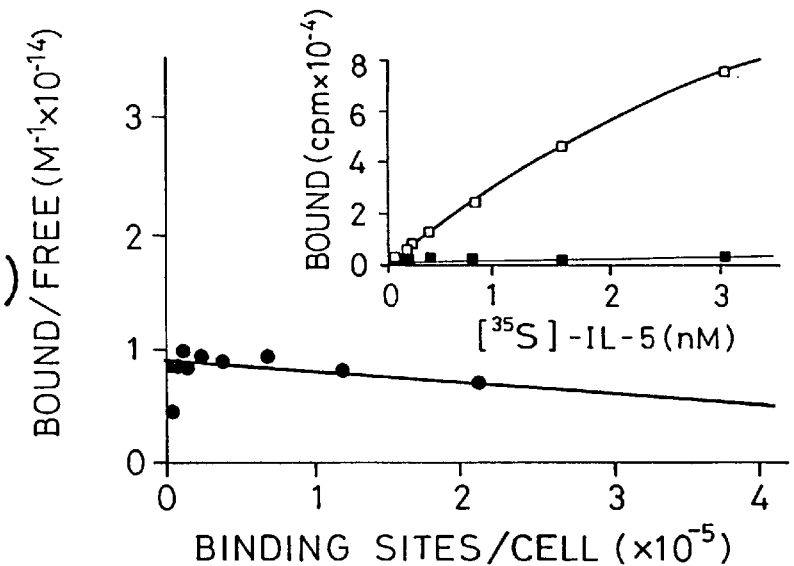
Figure 3C:
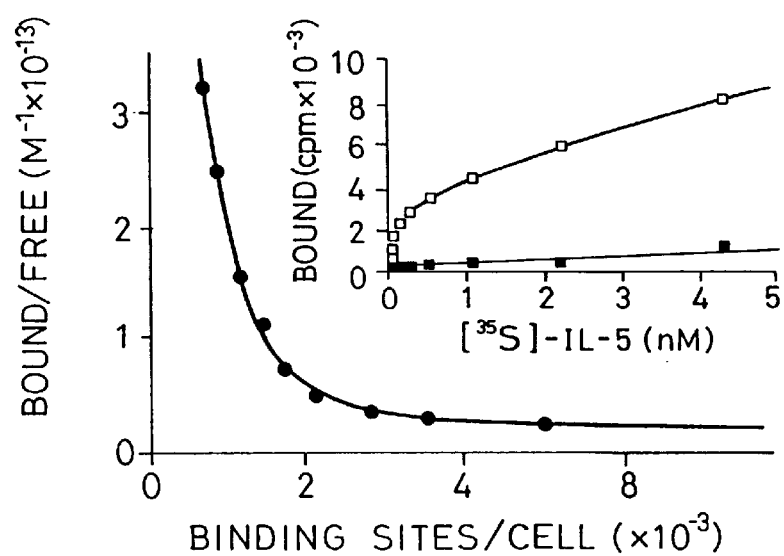

FIGS. 3(A), (B), (C) shows the Scatchard plot analysis (Ann N.Y. Acad. Sci, 51: 660, 1949) of $^{35}$S-labeled IL-5 binding to IL-5R expressed on transfectants and Y16 cells. The inset shows the direct binding data (□: total binding, ■:

non-specific binding). FIG. 3(A) shows the results when COS7 cells were transfected with pIL-5R.8: the dissociation constant was 2 nM and the number of the IL-5 binding was 12,000/cell. FIG. 3(B) shows the results when COS7 cells were transfected with pCAGGS.5R.8: the dissociation constant was 9.6 nM and the number of the IL-5 binding was 880,000/cell. FIG. 3(C) shows the results when Y16 cells were also tested for the IL-5 binding. A high affinity IL-5R and a low affinity IL-5R were found in the Y16 cells. The high affinity IL-5R has the number of IL-5 binding of 1,200/cell with the dissociation constant ($K_D$) of 20 pM. The low affinity IL-5R has the number of IL-5 binding of 22,000/cell with the dissociation constant ($K_D$) of 5.1 nM. These results suggest that the inserted IL-5R cDNA encodes a low affinity IL-5 recepter.

Cross-linking Test of Low Affinity IL-5R to IL-5 (Murine)

Because COS7 cells transfected with pCAGGS.5R.8 were found to express IL-5R at a higher level than those transfected with pIL-5R.8, pCAGGS.5R.8 was used for the following experiments.

COS7 cells ($1 \times 10^5$) were transfected with pCAGGS or pCAGGS5R.8 and the transformants were incubated with 4 nM $^{35}$S-labeled IL-5 in the presence or absence of 100-fold excess of non-labeled IL-5 as follows: a pCAGGS transformant without non-labeled IL-5 (lane 1), a pCAGGS transformant with non-labeled IL-5 (lane 2), a pCAGGS5R.8 transformant without non-labeled IL-5 (lane 3, 5), a pCAGGS5R.8 transformant with non-labeled IL-5 (lane 4, 6). The mixture was incubated at 37° C. for 10 minutes. Cells were washed extensively and then disuccinimidyl tartarate (DST)(Piece Chemical, Rockford, Ill.) was added to the cell suspension. The cell suspension was incubated at 4° C. for 30 minutes and then 1% Triton X-100 was added to the suspension to disrupt the cells. The disrupted cell suspension was loaded on a 7.5% SDS-polyacrylamide gel in the reducing (lane 5, 6) or non-reducing (lane 1–4) conditions.

Figure 4:
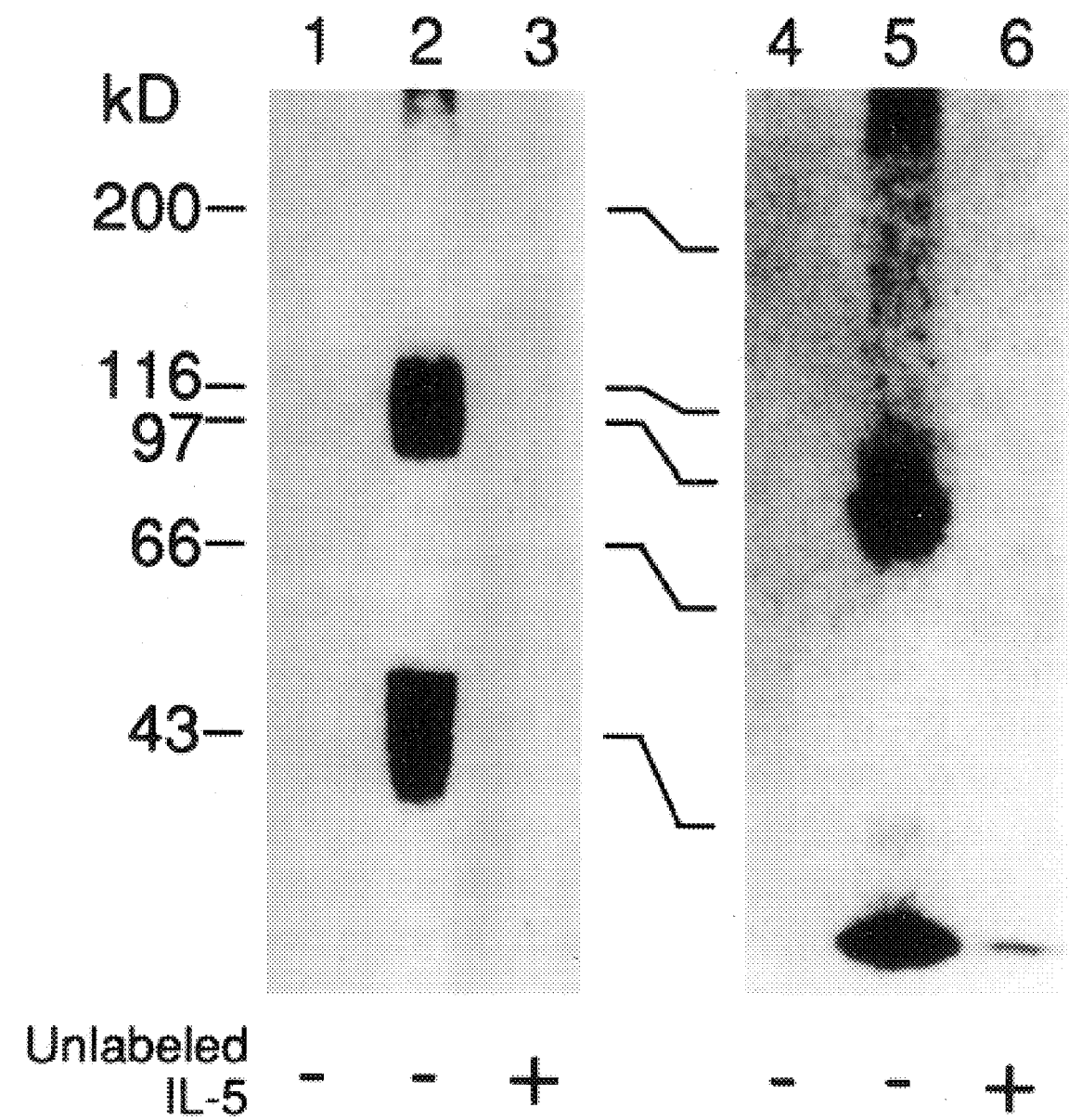
FIG. 4 shows the results of cross-linking experiment using $^{35}$S-labeled IL-5.

After electrophoresis, the gel was analyzed with Bio-Analyzer 100 (Fuji Film). The results are shown in FIG. 4. A band of approximately 90–100 KD in size was found which could be a low affinity IL-5R previously reported by Mita, et al., in Proc. Natl. Acad. Sci. U.S.A. 86: 2311, 1989. In contrast, the molecular weight of the band in the reducing condition was about 75 KD (lane 5 in FIG. 4). The difference was due to the dissociation of monomeric $^{35}$S-labeled IL-5 (MW:22,000) from the IL-5-IL-5R complex, because biologically active IL-5 binds to its receptor as a disulfide-linked dimer.

Immunoprecipitation of IL-5R expressed on pCAGGS.5R.8 Transfected COS7 (Murine)

Figure 5:
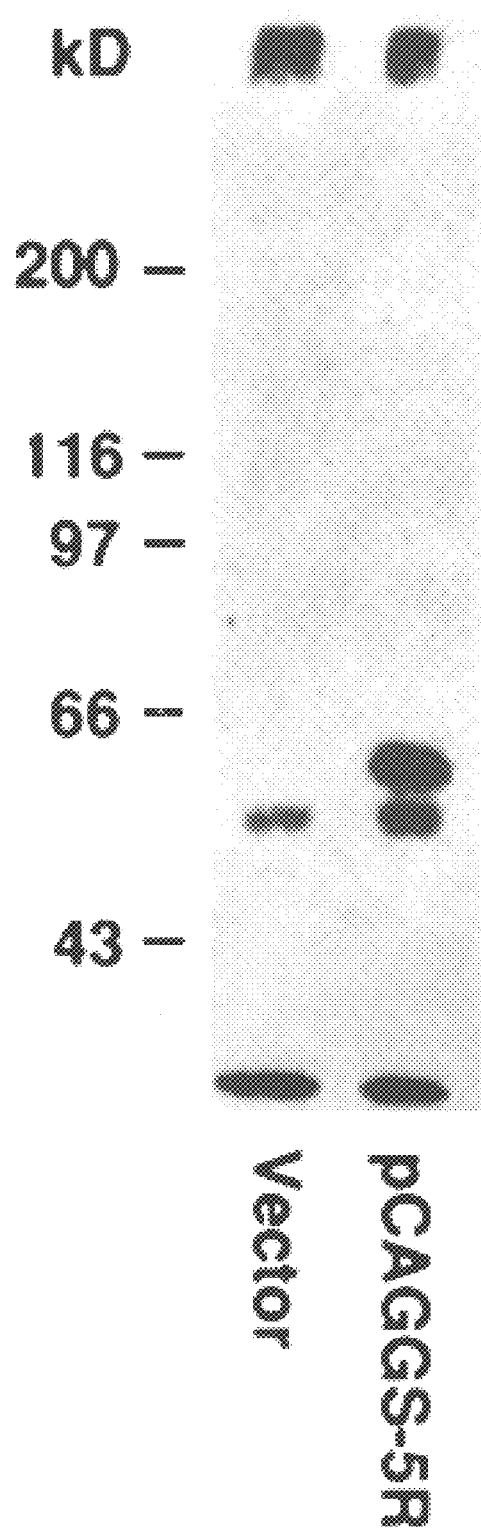
FIG. 5 shows the results of immunoprecipitation of the translated product of mouse IL-5RcDNA that codes for membrane type IL-5R.

The surfaces of the pCAGGS.5R.8 transfected COS7 ($5 \times 10^6$) cells were labeled with $^{125}$I using Iodobeads (Pierce Chemical, Rockford, Ill.). The cell was disrupted and H7 antibody was added to the cell lysate. Protein G-Sepharose (Pharmacia, Piscataway, N.J.) was added to the mixture and the mixture was incubated at 4° C. for 12 hours. The proteins adsorbed on the Sepharose was loaded on the SDS-PAGE. After electrophoresis under a reducing condition, the gel was analyzed with Bio-Analyzer 100. The band (MW: about 60 KD) was found only in the lane where the sample was prepared from the cell transfected with pCAGGS.5R.8 (FIG. 5).

Purification and Amino acid Sequence Analysis of Secretory IL-5R (Murine)

The IL-5R cDNA fragment obtained by XhoI digestion of pIL-5R.2 was inserted into pCAGGS vector by the similar method as in the case of pIL-5R.8 and the construct was designated as pCAGGS.5R.2. E. coli was transformed with the pCAGGS.5R.2 and the transformant was designated as E. coli 5R.2. E. coli 5R.2 was deposited with Fermentation Research Institute, Agency of Industrial Science and Technology Ministry of International Trade and Industry at 1–3 Higashi 1-Chome, Tsukuba-shi Ibaraki-ken 305 Japan, International Depository Authority and was assigned the accession number FERM BP 3084.

COS7 cells were transfected with pCAGGS.5R2 DNA according to the DEAE dextran method and was cultured in serum free medium (Iscove's DMEM) for two days. The culture supernatant was concentrated and the concentrate was electrophoresed on SDS-PAGE. A band (MW: approximately 50,000) was found in the lane on which the culture supernatant of pCAGGS.5R.2 transfected COS7 was loaded, while no band was found in the lane on which the culture supernatant of the pCAGGS vector alone was loaded. The culture supernatant of the pCAGGS.5R.2 transfected COS7 was loaded onto a column filled with H7 anibodies bound glycosylhard-gel (Seikagaku Kogyo, Tokyo). The column was washed with 2 mM HEPES solution containing 0.1% CHAPS and then H7 bound fractions were eluted out with 350 mM acetic acid. The fractions were lyophilized and then solubilized in a sample buffer for SDS-PAGE. The mixture was electrophoresed according to the method described by Laemmli in Nature 227: 680, 1970. The protein on the gel was transferred to a polyvinylidene difluoride membrane (Millipore, Bedford, Mass.) according to the electroblotting method. The band corresponding to a molecular weight of about 50,000 was cut out of the membrane and analyzed with a gas phase sequencer 447A (with HPLC system, Applied Biosystem Co.). The amino acid sequence of the N terminus of secretory IL-5R was as follows: Asp-Leu-Leu-Asn-His-Lys-Lys-Phe-Leu-Leu-Leu-Pro-Pro-Val-X-Phe-Thr-Ile-Lys-Ala. This amino acid sequence was found to be the same one (amino acid number 18–37) deduced from the nucleotide sequence of pIL-5R.8, membrane bound IL-5R cDNA clone. The amino acid sequence (amino acid number 1–17) is believed to be a signal peptide. X (amino acid number 15) may be Asn, which is deduced from the nucleotide sequence of cDNA, and to which a N-linked oligosaccharide is believed to bind.

The following Examples are described for human IL-5R.

Preparation of human Poly(A)$^+$ RNA

Eosinophils were obtained from 28 liter of peripheral blood of healthy volunteers and 50 ml of peripheral blood of a patient with eosinophilia. After removing erythrocytes, fractions containing eosinophils (1.09 g/ml) were collected from each sample by a density gradient centrifugation using Ficoll. The fraction contained 50% eosinophils and the number of eosinophis was $2.8 \times 10^9$ [healthy volunteers (helv)] and $2.0 \times 10^9$ [eosinophilia (eosi)]. 5 μg of poly(A)$^+$ RNA was recovered from each cell source as described above.

Construction of Human IL-5R cDNA Library

5 μg of each poly(A)$^+$ RNA thus obtained was used to synthesize cDNA (helv-cDNA, eosi-cDNA) as described above. The helv-cDNA was ligated to a BstXI linker and a fragment of helv-cDNA-linker complex having a size of 1,000 bp or more was selected. The fragment was then inserted into a BstXI digested pAGS-3 vector. E. coli MC1061 was transformed with the recombinant plasmid and about one million transformants were obtained (helv-cDNA library). The eosi-cDNA was ligated to a EcoRI linker and fragments of eosi-cDNA-linker complex having a size of 1,000 bp or more were selected. The fragments were inserted into a EcoRI digested λgt10 vector. E. coli C600Hfl was infected with the recombinant phage and 1.6 million independent plaques were obtained (eosi-cDNA library).

Screening of helv- and eosi-cDNA libraries according to the colony-hybridization method The helv-cDNA library was screened according to the colony hybridization method. One million colonies of the helv-cDNA library were grown on a solid medium and the colonies were transferred to 100 sheets of nitrocellulose membranes (8 cm in diameter). After DNA fixation, the membrane was placed in a bag containing 10×Denhardt's solution, 6×SSC (0.9M NaCl, 0.09M sodium citrate), 100 µg/ml of heat-denatured salmon sperm DNA. The $^{32}$P -labeled, 1.2 kb HindIII-PstI fragment of pIL-5R.8 was added to the bag and hybridization was carried out at 65° C. for 24 hours under less stringent conditions. The membrane was washed at 45° C. in a solution containing 1×SSC and 0.1% SDS. After washing, a X-ray film was overlayed on the membrane for autoradiography as described above. A positive clone was obtained and was designated as ph5R.1. However, the cDNA fragment of ph5R.1 was found to contain only 1.0 kb, which was not an right size for IL-5R. Subsequently, the eosi-cDNA library was screened using the XhoI digested, 1.0 kb fragment of ph5R.1 as a probe according to the protocol of Colony/Plaque Screen. Approximately one million clones of the eosi-cDNA library was grown on a solid medium and the plaques were transferred to nylon membranes (13 cm in diameter, Colony/Plaque Screen, Dupont-NEN, Boston, Mass.). Hybridization was carried out at 65° C. for 24 hours in a solution containing 1% SDS, 1M NaCl, 10% Dextran sulfate, 100 µg/ml of heat-denatured salmon sperm DNA. After hybridization, the membrane was washed at 65° C. for an hour in a solution containing 2×SSC and 1% SDS. Two positive clones containing about 2 kb cDNA fragment were obtained and designated as HSIL5R and HSIL5R2.

E. coli was transformed with HSIL5R or HSIL5R2 and the transformants were designated as E. coli HSIL5R or E. coli HSIL5R2, respectively.

The transformants were deposited with Fermentation Research Institute, Agency of Industrial Science and Technology Ministry of International Trade and Industry at 1–3 Higashi 1-Chome, Tsukuba-shi Ibaraki-ken 305 Japan, International Depository Authority and were assigned the accession number as follows:

|  | Accession No. |
| --- | --- |
| E. coli HSIL5R | FERM BP-3542 |
| E. coli HSIL5R2 | FERM BP-3543 |

DNA Sequence Analysis of HILS5R and HSIL5R2

HILS5R and HSIL5R2 were digested with EcoRI, and the EcoRI digested IL-5R fragment was inserted into the EcoRI site of Bluescript KS(-) vector (Stratagene, La Jolla, Calif.). The nucleotide sequence was determined according to the Sanger's method. The sequence was determined in both 5' and 3' direction. Initial primers were synthesized according to the sequence of the 5' upstream of the IL-5R cDNA fragment (T3 primer) and of the 3' downstream of the IL-5R cDNA fragment (T7 primer). After the 5' and 3' end sequences were determined, subsequent primers were synthesized according the sequence analyzed by the DNA sequencing. The nucleotide sequence thus determined was found to be complementary.

SEQ ID No.17 shows the nucleotide and the corresponding amino acid sequence of HSIL5R. Amino acids 1–20 are hypothetically a signal peptide and amino acids 345–365 one believed to be a transmembrane region according to hydropathy plot. These assumption are based on the same model as those of mouse. Amino acids 35–37, 131–133, 137–139, 142–144, 216–218 and 244–246 seem to be the region for N-linked oligosacchride binding. The estimated molecular weight (45,556) of IL-5R from cDNA clone differs from the real molecular weight (about 60,000) of IL-5R produced by the transformed COS7 cell. The difference of the weight may be due to the N-linked oligosaccharide. The nucleotide sequence downstream of the symbol nucleotide 1184 distinguishs HSIL5R (SEQ ID No.17) from HSIL5R2 (SEQ ID No. 18).

SEQ ID No.18 shows the nucleotide and the corresponding amino acid sequence of HSIL5R2. The amino acid sequence of HSIL5R2 terminates at Ile (amino acid number 396), while HSIL5R contains additional 24 amino acids following Ser at amino acid No. 396. The amino acid sequences of HSIL5R and HSIL5R2 are identical from Met (amino acid number 1) to Gly (amino acid number 395) except for an amino acid at position 129 where the amino acid is Val on the sequence of HSIL5 and Ile on the sequence of HSIL5R2.

Expression of human IL-5R on COS7 and Cross-linking experiment

The Bluescript kS (−) recombinant was digested with EcoRI. The restriction fragments containing IL-5R of HSIL5R and HSIL5R2 were inserted into pCAGGS. The resulting constructs were designated as pCAGGS.HS.IL-5R and pCAGGS.HSIL5R2. COS7 cells were transfected with these recombinant DNAs and the transformed cells were tested for their chemical characteristics using $^{35}$S-labeled murine IL-5 or $^{125}$I-labeled human IL-5 (2×10$^6$ cpm/µg) according to the cross-linking method.

Figure 7:
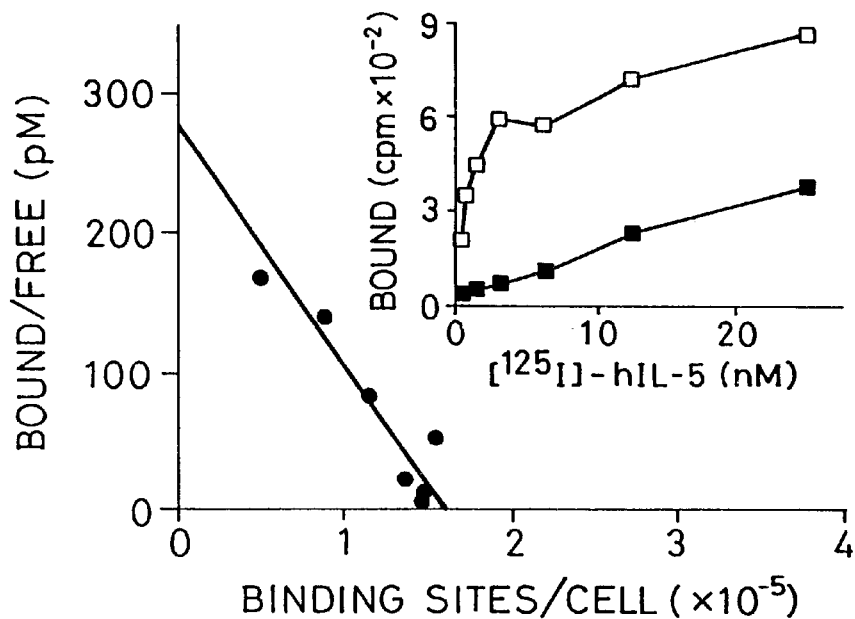
FIGS. 7A–7D shows Scatchard plot analyses of a binding assay of $^{35}$S-labeled murine IL-5 or $^{125}$I labeled human IL-5 to the pCAGGS.HSIL5R or pCAGGS.HSIL5R2 transfected COS 7 cell. The symbol □ represents a total binding and the symbol ■ represents a nonspecific binding in the presence of a 100-fold excess of non-radiolabeled IL-5. COS 7 cells were transfected with pCAGGS.HSIL5R and the transformant was tested for binding using $^{125}$I-labeled human IL-5 (FIG. 7A, inset of FIG. 7A). COS 7 cells were transfected with pCAGGS.HSIL5R2 and the transformant was tested for binding using $^{125}$I-labeled human IL-5 (FIG. 7B, inset of FIG. 7B). COS 7 cells were transfected with pCAGGS.HSIL5R and the transformant was tested for binding using $^{35}$S-labeled mouse IL-5 (FIG. 7C, inset of FIG. 7C). COS 7 cells were transfected with pCAGGS.HSIL5R2 and the transformant was tested for binding using $^{35}$S-labeled mouse IL-5 (FIG. 7D, inset of FIG. 7D).
Figure 7:
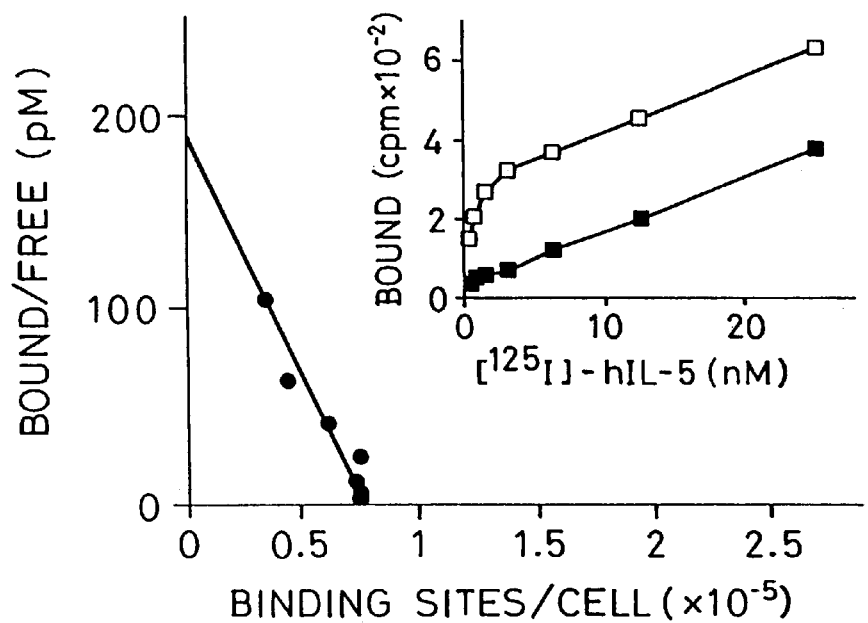
Figure 7:
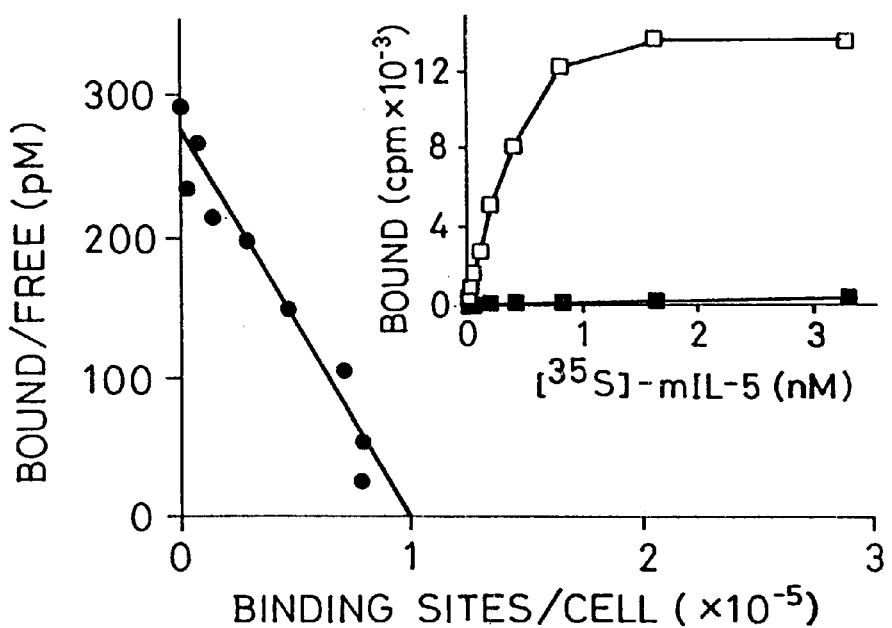
Figure 7:
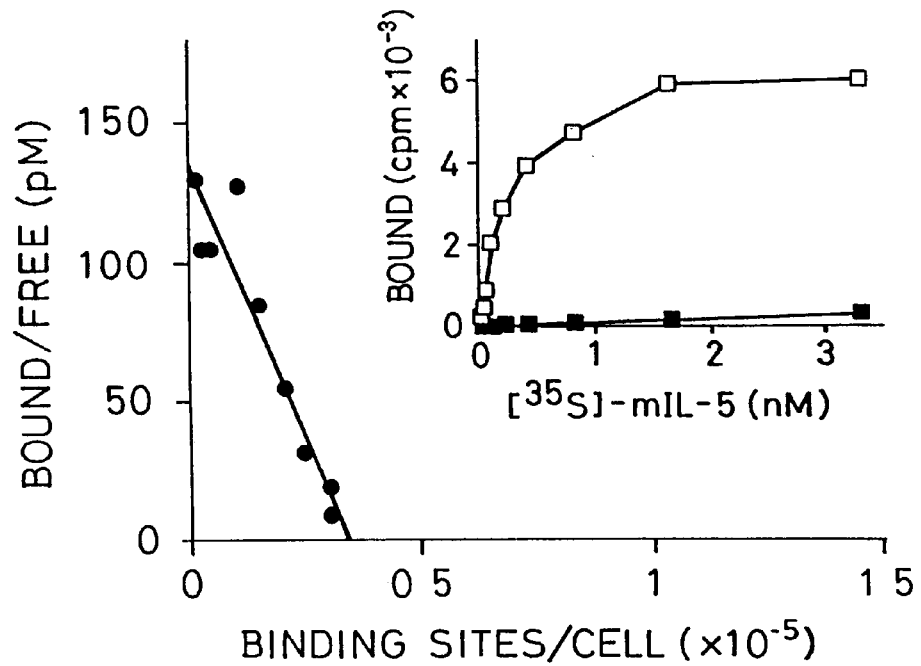

Binding of $^{125}$I-labeled human IL-5 to IL-5R expressed on the COS7 cell (pCAGGS.HSIL5R transformant) was shown in the inset of FIG. 7A, and the results analyzed by Scatchard plot was shown in FIG. 7A. Binding of $^{125}$I-labeled human IL-5 to IL-5R expressed on COS7 cell (pCAGGS.HSIL5R2 transformant) was shown in the inset of FIG. 7B, and the results analyzed by Scatchard plot was shown in FIG. 7B. Binding of $^{35}$S-labeled murine IL-5 to IL-5R expressed on the COS7 cells (pCAGGS.HSIL5R transformant) was shown in the inset of FIG. 7C, and the results analyzed by Scatchard plot was shown in FIG. 7C. Binding of $^{35}$S-labeled murine IL-5 to IL-5R expressed on COS7 cell (pCAGGS.HSIL5R2 transformant) was shown in the inset of FIG. 7D, and the results analyzed by Scatchard plot were shown in FIG. 7D.

A high affinity IL-5R with the dissociation constant ($K_D$) of less than 100 pM was not detectable by $^{125}$I-labeled human IL-5 because of poor specific radioactivity. To calculate the dissociation constant of a high affinity IL-5R, we used $^{35}$S-labeled mouse IL-5 which has high specific radioactivity and is not denatured. The dissociation constant of the pCAGGS.HSIL5R transfected COS7 cells were about 590 pM when radiolabeled human IL-5 was used, while the dissociation constant of the same pCAGGS.HSIL5R transfected COS7 cells were about 250 pM when radiolabeled mouse IL-5 was used. The dissociation constant of the pCAGGS.HSIL5R2 transfected COS7 cells were about 410 pM with radiolabeled human IL-5, while the dissociation constant of the same pCAGGS.HSIL5R2 transfected COS7 cells were about 355 pM when radiolabeled mouse IL-5 was used. These results are comparable to the dissociation constant (170–330 pM) of eosinophils from healthy adult peripheral blood that we reported previously. The data of the previous report were calculated by Scatchard analysis of binding assays using $^{35}$S-labeled mouse IL-5.

The dissociation constant thus determined was higher than that of mouse low affinity IL-5R and fell into the average value of normal human eosinophils. Taken altogether, the isolated IL-5R cDNA fragment was expressed on the surface of the COS7 cells and the IL-5R expressed on the cell surface are responsible for the binding of human IL-5.

Figure 8:
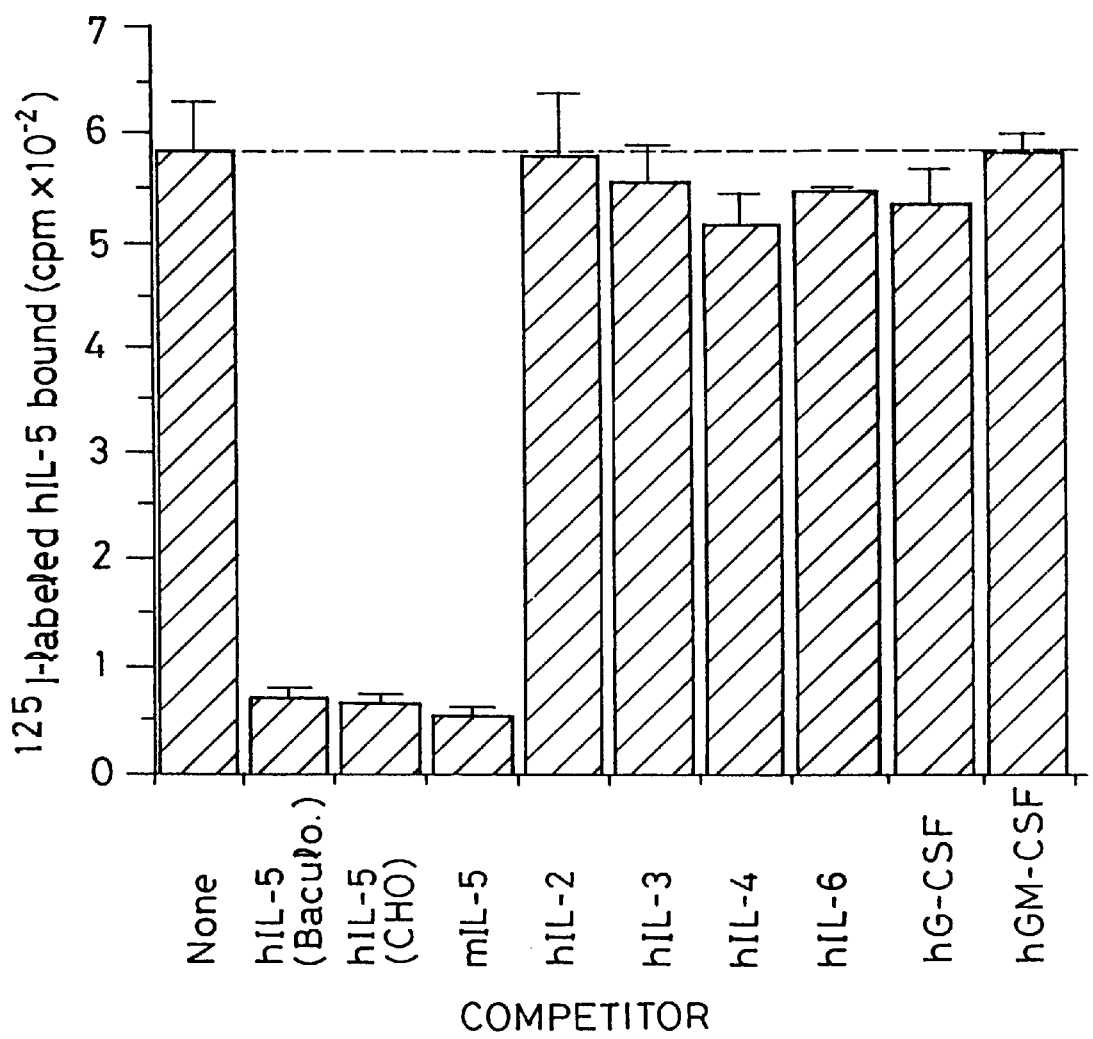
FIG. 8 is a bar graph showing the binding specificity of $^{125}$I labeled human IL-5 to IL-5R. 100 μl of the COS 7 transformants (4×10$^5$ cells) carrying pCAGGS.HSIL5R and 500 pM $^{125}$I-labeled human IL-5 were incubated in the presence of a 1,000-fold excess of cytokines.

FIG. 8 shows inhibitory effects of cytokines on the binding of IL-5 to IL-5R. IL-5R expressed on the COS7 transformants specifically binds to human and mouse IL-5 but not to human IL-2, human IL-3, human IL-4, human IL-6, human GM-CSF or human G-CSF.

Cross-linking of Radiolabeled IL-5 to the COS7 Transformants

The COS7 transformant ($1 \times 10^5$ cells) carrying pCAGGS.HSIL5R or pCAGGS.HSIL5R2 and either 5.5 nM $^{35}$S-labeled mouse IL-5 or 1 nM $^{125}$I-labeled human IL-5 were mixed in the presence or absence of 250-fold excess of non-labeled IL-5. After one hour incubation at 4° C., 1 mM bis(sulfosuccinimidyl) suberate (Pierce Chemical Co., Rockford, Ill.) was added to the mixture. The mixture was further incubated at 4° C. for 30 minutes. After the incubation, binding was analyzed as described above.

Figure 9:
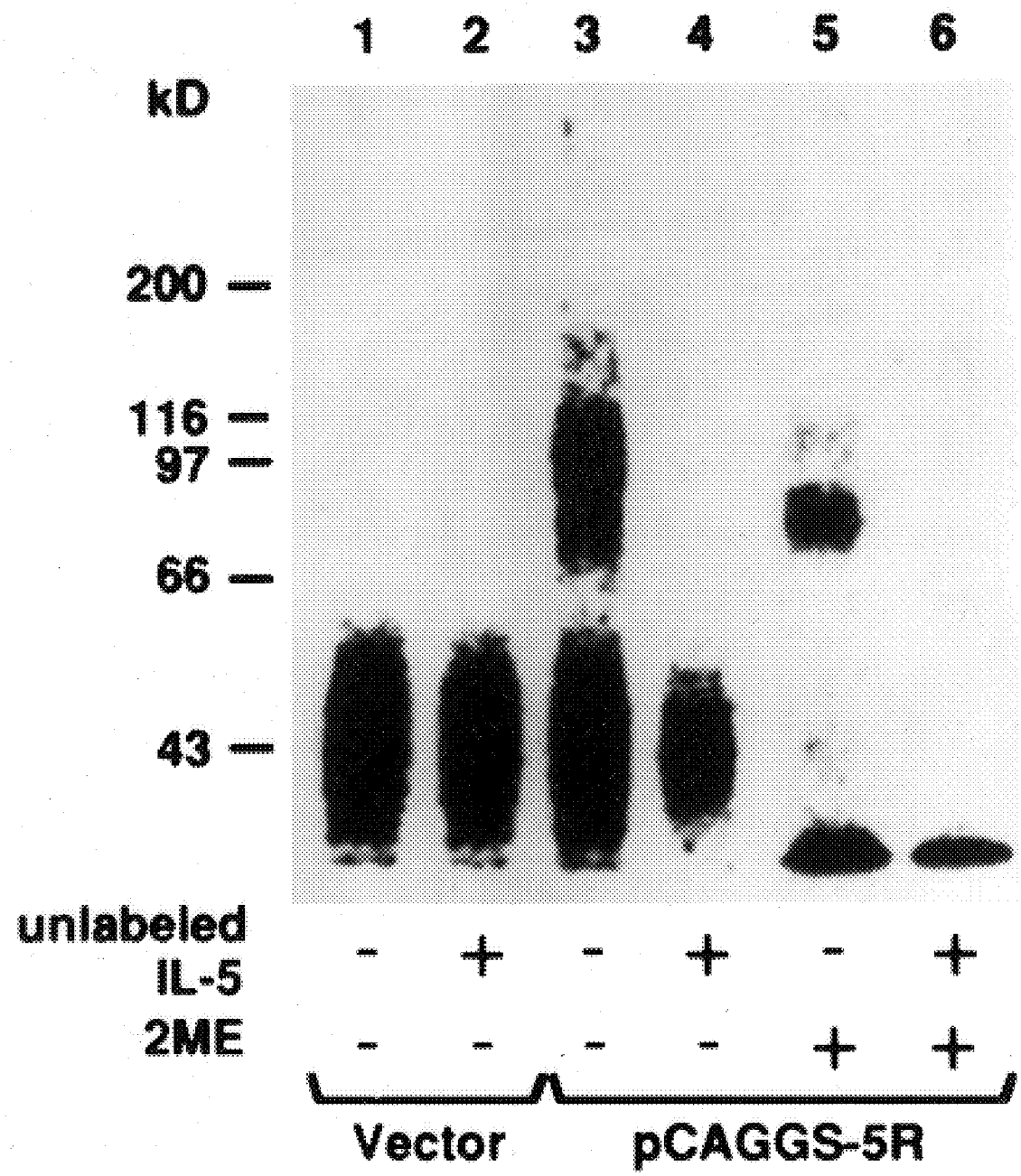
FIG. 9 shows a band pattern of chemical cross-linking of IL-5 analysed by SDS-PAGE. COS cells were transfected with a pCAGGS vector and the transformant was incubated with $^{35}$S-labeled murine IL-5 (lane 1) or $^{125}$I-labeled human IL-5 (lane 4). Then a cross-linking agent, bis (sulfosuccinimidyl) suberate was added to the mixture. After incubation, the mixture was electrophoresed under non-reduced condition. Similarly, COS7 cells were transfected with pCAGGS. HSIL5R and the transformants were incubated with $^{35}$S-labeled murine IL-5 in the presence (lane 3) or absence (lane 2) of an excess amount of non-labeled murine IL-5 or with $^{125}$I-labeled human IL-5 in the presence (lane 6) or absence(lane 5) of an excess amount of non-labeled human IL-5. Then, a cross-linking agent, bis (sulfosuccinimidyl) suberate was added to the mixture. After incubation, the mixture was electrophoresed under non-reducing condition.

In FIG. 9, COS7 cells transfected with a PCAGGS vector alone or pCAGGSHSIL5R were incubated with $^{35}$S-labeled murine IL-5 (A; lane 1, 2, 3) or $^{125}$I-labeled human IL-5 (B; lane 4, 5, 6). COS7 cells transfected with a pCAGGS.HSIL5R were incubated with $^{35}$S-labeled murine IL-5 in the presence (lane 3) or absence (lane 2) of 250-fold excess of non-labeled IL-5, or were incubated with $^{125}$I-labeled human IL-5 in the presence (lane 6) or absence (lane 5) of 250-fold excess amount of non-labeled IL-5.

There were two bands corresponding to about 105 kD (lane 2) and 86 kD (lane 5). Since murine IL-5 is 45 kD and human IL-5 is 31 kD, the molecular weight of human IL-5R could be estimated to be 55,000–60,000. This molecular weight of human IL-5R is almost the same as that of IL-5R expressed on eosinophils as we reported previously (Cellular Immunology, 133; 484–469). In the presence of a 250-fold excess of non-labeled IL-5, no band was found (lanes 3, 6 in FIG. 9).

Same experiment was carried out using pCAGGS.HSIL5R2 and the results were very similar to that described above.

What is claimed is:

1. An isolated cDNA sequence coding for interleukin 5 receptor wherein the amino acid sequence comprises the sequence described in SEQ ID NO. 13 or 14.

2. The isolated cDNA sequence of claim 1 wherein the nucleotide sequence described in SEQ ID No. 9 comprises the open reading frame sequence coding for human interleukin 5 receptor.

3. The isolated cDNA sequence of claim 1 wherein the nucleotide sequence described in SEQ ID No. 10 comprises the entire sequence coding for human interleukin 5 receptor.

4. The isolated cDNA sequence of claim 1 wherein the nucleotide sequence described in SEQ ID No. 11 comprises the open reading frame sequence coding for human interleukin 5 receptor 2.

5. The isolated cDNA sequence of claim 1 wherein the nucleotide sequence described in SEQ ID No. 12 comprises the entire sequence coding for human interleukin 5 receptor 2.

6. The isolated cDNA sequence coding for secretory human interleukin 5 receptor which lacks a cytoplasmic region and has binding specificity for interleukin 5 and comprises amino acids 1 to 333 of SEQ ID NO. 13 or 14.

7. An expression vector comprising the cDNA sequence of any one of claims 1, 2, 3, 4, 5, and 6.

8. A transfectant which is obtained by transfecting the expression vector of claim 7 into a host cell.

9. A method of producing a secretory human interleukin 5 receptor which comprises culturing a cell capable of expressing human interleukin 5 receptor having an amino acid sequence comprising amino acids 1 to 333 of SEQ ID NO. 13 or 14 in a medium and isolating the human interleukin 5 receptor from the culture supernatant using an interleukin 5 receptor antibody.

10. A method of producing a human interleukin 5 receptor, which comprises culturing a cell capable of expressing human interleukin 5 receptor having an amino acid sequence comprising amino acids 1 to 333 of SEQ ID NO. 13 or 14 in a medium and isolating the human interleukin 5 receptor from the cells or the culture supernatant.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1245 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATGGTGCCTG TGTTACTAAT TCTTGTGGGA GCTTTGGCAA CACTGCAAGC TGACTTACTT        60

AATCACAAAA AGTTTTTACT TCTACCACCT GTCAATTTTA CCATTAAAGC CACTGGATTA       120

GCTCAAGTTC TTTTACACTG GGACCCAAAT CCTGACCAAG AGCAAAGGCA TGTTGATCTA       180

GAGTATCACG TGAAAATAAA TGCCCCACAA GAAGACGAAT ATGATACCAG AAAGACTGAA       240

AGCAAATGTG TGACCCCCCT TCATGAAGGC TTTGCAGCTA GCGTGAGGAC CATTCTGAAG       300

AGCAGCCATA CAACTCTGGC CAGCAGTTGG GTTTCTGCTG AACTCAAAGC TCCACCAGGA       360

TCTCCTGGAA CCTCGGTTAC GAATTTAACT TGTACCACAC ACACTGTTGT AAGTAGCCAC       420

ACCCACTTAA GGCCATACCA AGTGTCCCTT CGTTGCACCT GGCTTGTTGG GAAGGATGCC       480

CCTGAGGACA CACAGTATTT CCTATACTAC AGGTTTGGTG TTTTGACTGA AAAATGCCAA       540

GAATACAGCA GAGATGCACT GAACAGAAAT ACTGCATGCT GGTTTCCCAG ACATTTATC        600

AACAGCAAAG GGTTTGAACA GCTTGCTGTG CACATTAATG GCTCAAGCAA GCGTGCTGCA       660

ATCAAGCCCT TGATCAGCT GTTCAGTCCA CTTGCCATTG ACCAAGTGAA TCCTCCAAGG        720

AATGTCACAG TGGAAATTGA AAGCAATTCT CTCTATATAC AGTGGGAGAA ACCACTTTCT       780

GCCTTTCCAG ATCATTGCTT TAACTATGAG CTGAAAATTT ACAACACAAA AAATGGTCAC       840

ATTCAGAAGG AAAAACTGAT CGCCAATAAG TTCATCTCAA AAATTGATGA TGTTTCTACA       900

TATTCCATTC AAGTGAGAGC AGCTGTGAGC TCACCTTGCA GAATGCCAGG AAGGTGGGGC       960

GAGTGGAGTC AACCTATTTA TGTGGGAAAG GAAAGGAAGT CCTTGGTAGA ATGGCATCTC      1020

ATTGTGCTCC CAACAGCTGC CTGCTTCGTC TTGTTAATCT TCTCACTCAT CTGCAGAGTG      1080
```

| | |
|---|---|
| TGTCATTTAT GGACCAGGTT GTTTCCACCG GTTCCGGCCC CAAAGAGTAA CATCAAAGAT | 1140 |
| CTCCCTGTGG TTACTGAATA TGAGAAACCT TCGAATGAAA CCAAAATTGA AGTTGTACAT | 1200 |
| TGTGTGGAAG AGGTTGGATT TGAAGTCATG GGAAATTCCA CGTTT | 1245 |

(2) INFORMATION FOR SEQ ID NO:2:

(i) SEQUENCE CHARACTERISTICS:
    (A) LENGTH: 1808 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:2:

| | |
|---|---|
| GAAATAATTG GTAAACACAG AAAATGTTTC AATAGAAAAA AGAGGAAACA GAACACTGTG | 60 |
| TAGCCCTGTT ATCAGCAGAG ACAGAGCTAA CGCTGGGGAT ACCAAACTAG AAGAAGCTCA | 120 |
| CTGGACAGGT CCCGGTATGC AGTTCTATTT TTGTTGATGG CTCTGTATCT AATGTGTTCA | 180 |
| TTTGTACCAA GGATCTAACC AGGGTCTTCC AGAGTCTGAG CAAGCTTCTC CCACTGAGCT | 240 |
| ACATCACAGC CCCCTGTTTA TTGGAAGAAG AAATACTTAC ACCTTTCCAG TATTCGGCTA | 300 |
| CCATGGTGCC TGTGTTACTA ATTCTTGTGG GAGCTTTGGC AACACTGCAA GCTGACTTAC | 360 |
| TTAATCACAA AAAGTTTTTA CTTCTACCAC CTGTCAATTT TACCATTAAA GCCACTGGAT | 420 |
| TAGCTCAAGT TCTTTTACAC TGGGACCCAA ATCCTGACCA AGAGCAAAGG CATGTTGATC | 480 |
| TAGAGTATCA CGTGAAAATA AATGCCCCAC AAGAAGACGA ATATGATACC AGAAAGACTG | 540 |
| AAAGCAAATG TGTGACCCCC CTTCATGAAG GCTTTGCAGC TAGCGTGAGG ACCATTCTGA | 600 |
| AGAGCAGCCA TACAACTCTG GCCAGCAGTT GGGTTTCTGC TGAACTCAAA GCTCCACCAG | 660 |
| GATCTCCTGG AACCTCGGTT ACGAATTTAA CTTGTACCAC ACACACTGTT GTAAGTAGCC | 720 |
| ACACCCACTT AAGGCCATAC CAAGTGTCCC TTCGTTGCAC CTGGCTTGTT GGGAAGGATG | 780 |
| CCCCTGAGGA CACACAGTAT TTCCTATACT ACAGGTTTGG TGTTTTGACT GAAAAATGCC | 840 |
| AAGAATACAG CAGAGATGCA CTGAACAGAA ATACTGCATG CTGGTTTCCC AGGACATTTA | 900 |
| TCAACAGCAA AGGGTTTGAA CAGCTTGCTG TGCACATTAA TGGCTCAAGC AAGCGTGCTG | 960 |
| CAATCAAGCC CTTTGATCAG CTGTTCAGTC CACTTGCCAT TGACCAAGTG AATCCTCCAA | 1020 |
| GGAATGTCAC AGTGGAAATT GAAAGCAATT CTCTCTATAT ACAGTGGGAG AAACCACTTT | 1080 |
| CTGCCTTTCC AGATCATTGC TTTAACTATG AGCTGAAAAT TTACAACACA AAAAATGGTC | 1140 |
| ACATTCAGAA GGAAAAACTG ATCGCCAATA AGTTCATCTC AAAAATTGAT GATGTTTCTA | 1200 |
| CATATTCCAT TCAAGTGAGA GCAGCTGTGA GCTCACCTTG CAGAATGCCA GGAAGGTGGG | 1260 |
| GCGAGTGGAG TCAACCTATT TATGTGGGAA AGGAAAGGAA GTCCTTGGTA GAATGGCATC | 1320 |
| TCATTGTGCT CCCAACAGCT GCCTGCTTCG TCTTGTTAAT CTTCTCACTC ATCTGCAGAG | 1380 |
| TGTGTCATTT ATGGACCAGG TTGTTTCCAC CGGTTCCGGC CCCAAAGAGT AACATCAAAG | 1440 |
| ATCTCCCTGT GGTTACTGAA TATGAGAAAC CTTCGAATGA AACCAAAATT GAAGTTGTAC | 1500 |
| ATTGTGTGGA GAGGTTGGA TTTGAAGTCA TGGGAAATTC CACGTTTTGA TGGCATTTTG | 1560 |
| CCATTCTGAA ATGAACTCAT ACAGGACTCC GTGATAAGAG CAAGGACTGC TATTTCTTGG | 1620 |
| CAAGGAGGTA TTTCAAATGA ACACTCAGAG CCAGGCGGTG GTAGAGCTCG CCTTTAATAC | 1680 |
| CAGCACCTGG GATGCACAGA CGGGAGGATT TCTGAGTTCG AGGCCAGCTT GGTCTATAAA | 1740 |
| GTGAGTTCCA GGACAGCCAG AGCTACACAG AGAAACCCTG TCTCGAAAAA ACAAACAAAC | 1800 |

AAACAAAC                                                                1808

(2) INFORMATION FOR SEQ ID NO:3:

(i) SEQUENCE CHARACTERISTICS:
        (A) LENGTH: 996 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATGGTGCCTG TGTTACTAAT TCTTGTGGGA GCTTTGGCAA CACTGCAAGC TGACTTACTT      60

AATCACAAAA AGTTTTTACT TCTACCACCT GTCAATTTTA CCATTAAAGC CACTGGATTA     120

GCTCAAGTTC TTTTACACTG GGACCCAAAT CCTGACCAAG AGCAAAGGCA TGTTGATCTA     180

GAGTATCACG TGAAAATAAA TGCCCCACAA GAAGACGAAT ATGATACCAG AAAGACTGAA     240

AGCAAATGTG TGACCCCCCT TCATGAAGGC TTTGCAGCTA GCGTGAGGAC CATTCTGAAG     300

AGCAGCCATA CAACTCTGGC CAGCAGTTGG GTTTCTGCTG AACTCAAAGC TCCACCAGGA     360

TCTCCTGGAA CCTCGGTTAC GAATTTAACT TGTACCACAC ACACTGTTGT AAGTAGCCAC     420

ACCCACTTAA GGCCATACCA AGTGTCCCTT CGTTGCACCT GGCTTGTTGG GAAGGATGCC     480

CCTGAGGACA CACAGTATTT CCTATACTAC AGGTTTGGTG TTTTGACTGA AAAATGCCAA     540

GAATACAGCA GAGATGCACT GAACAGAAAT ACTGCATGCT GGTTTCCCAG GACATTTATC     600

AACAGCAAAG GGTTTGAACA GCTTGCTGTG CACATTAATG GCTCAAGCAA GCGTGCTGCA     660

ATCAAGCCCT TTGATCAGCT GTTCAGTCCA CTTGCCATTG ACCAAGTGAA TCCTCCAAGG     720

AATGTCACAG TGGAAATTGA AAGCAATTCT CTCTATATAC AGTGGGAGAA ACCACTTTCT     780

GCCTTTCCAG ATCATTGCTT TAACTATGAG CTGAAAATTT ACAACACAAA AAATGGTCAC     840

ATTCAGAAGG AAAAACTGAT CGCCAATAAG TTCATCTCAA AAATTGATGA TGTTTCTACA     900

TATTCCATTC AAGTGAGAGC AGCTGTGAGC TCACCTTGCA GAATGCCAGG AAGGTGGGGC     960

GAGTGGAGTC AACCTATTTA TGTGGAAACC TTCGAA                              996

(2) INFORMATION FOR SEQ ID NO:4:

(i) SEQUENCE CHARACTERISTICS:
        (A) LENGTH: 1355 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TATTCGGCTA CCATGGTGCC TGTGTTACTA ATTCTTGTGG GAGCTTTGGC AACACTGCAA      60

GCTGACTTAC TTAATCACAA AAAGTTTTTA CTTCTACCAC CTGTCAATTT TACCATTAAA     120

GCCACTGGAT TAGCTCAAGT TCTTTTACAC TGGGACCCAA ATCCTGACCA AGAGCAAAGG     180

CATGTTGATC TAGAGTATCA CGTGAAAATA AATGCCCCAC AAGAAGACGA ATATGATACC     240

AGAAAGACTG AAAGCAAATG TGTGACCCCC CTTCATGAAG GCTTTGCAGC TAGCGTGAGG     300

ACCATTCTGA GAGCAGCCA TACAACTCTG GCCAGCAGTT GGGTTTCTGC TGAACTCAAA     360

GCTCCACCAG GATCTCCTGG AACCTCGGTT ACGAATTTAA CTTGTACCAC ACACACTGTT     420

GTAAGTAGCC ACACCCACTT AAGGCCATAC CAAGTGTCCC TTCGTTGCAC CTGGCTTGTT     480

GGGAAGGATG CCCCTGAGGA CACACAGTAT TTCCTATACT ACAGGTTTGG TGTTTTGACT     540

-continued

```
GAAAAATGCC AAGAATACAG CAGAGATGCA CTGAACAGAA ATACTGCATG CTGGTTTCCC      600

AGGACATTTA TCAACAGCAA AGGGTTTGAA CAGCTTGCTG TGCACATTAA TGGCTCAAGC      660

AAGCGTGCTG CAATCAAGCC CTTTGATCAG CTGTTCAGTC CACTTGCCAT TGACCAAGTG      720

AATCCTCCAA GGAATGTCAC AGTGGAAATT GAAAGCAATT CTCTCTATAT ACAGTGGGAG      780

AAACCACTTT CTGCCTTTCC AGATCATTGC TTTAACTATG AGCTGAAAAT TTACAACACA      840

AAAAATGGTC ACATTCAGAA GGAAAAACTG ATCGCCAATA AGTTCATCTC AAAAATTGAT      900

GATGTTTCTA CATATTCCAT TCAAGTGAGA GCAGCTGTGA GCTCACCTTG CAGAATGCCA      960

GGAAGGTGGG GCGAGTGGAG TCAACCTATT TATGTGGAAA CCTTCGAATG AAACCAAAAT     1020

TGAAGTTGTA CATTGTGTGG AAGAGGTTGG ATTTGAAGTC ATGGGAAATT CCACGTTTTG     1080

ATGGCATTTT GCCATTCTGA AATGAACTCA TACAGGACTC CGTGATAAGA GCAAGGACTG     1140

CTATTTCTTG GCAAGGAGGT ATTTCAAATG AACACTCAGA GCCAGGCGGT GGTAGAGCTC     1200

GCCTTTAATA CCAGCACCTG GGATGCACAG ACGGGAGGAT TTCTGAGTTC GAGGCCAGCT     1260

TGGTCTATAA AGTGAGTTCC AGGACAGCCA GAGCTACACA GAGAAACCCT GTCTCGAAAA     1320

AACAAACAAA CAAACAAACA AACAAAAATG AACAC                               1355
```

(2) INFORMATION FOR SEQ ID NO:5:

(i) SEQUENCE CHARACTERISTICS:
        (A) LENGTH: 415 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:5:

```
Met Val Pro Val Leu Leu Ile Leu Val Gly Ala Leu Ala Thr Leu Gln
1               5                   10                  15

Ala Asp Leu Leu Asn His Lys Lys Phe Leu Leu Pro Pro Val Asn
            20                  25                  30

Phe Thr Ile Lys Ala Thr Gly Leu Ala Gln Val Leu Leu His Trp Asp
        35                  40                  45

Pro Asn Pro Asp Gln Glu Gln Arg His Val Asp Leu Glu Tyr His Val
    50                  55                  60

Lys Ile Asn Ala Pro Gln Glu Asp Glu Tyr Asp Thr Arg Lys Thr Glu
65                  70                  75                  80

Ser Lys Cys Val Thr Pro Leu His Glu Gly Phe Ala Ala Ser Val Arg
                85                  90                  95

Thr Ile Leu Lys Ser Ser His Thr Thr Leu Ala Ser Ser Trp Val Ser
            100                 105                 110

Ala Glu Leu Lys Ala Pro Pro Gly Ser Pro Gly Thr Ser Val Thr Asn
        115                 120                 125

Leu Thr Cys Thr Thr His Thr Val Val Ser Ser His Thr His Leu Arg
130                 135                 140

Pro Tyr Gln Val Ser Leu Arg Cys Thr Trp Leu Val Gly Lys Asp Ala
                145                 150                 155                 160

Pro Glu Asp Thr Gln Tyr Phe Leu Tyr Tyr Arg Phe Gly Val Leu Thr
                165                 170                 175

Glu Lys Cys Gln Glu Tyr Ser Arg Asp Ala Leu Asn Arg Asn Thr Ala
            180                 185                 190

Cys Trp Phe Pro Arg Thr Phe Ile Asn Ser Lys Gly Phe Glu Gln Leu
        195                 200                 205
```

-continued

```
Ala Val His Ile Asn Gly Ser Ser Lys Arg Ala Ala Ile Lys Pro Phe
    210                 215                 220
Asp Gln Leu Phe Ser Pro Leu Ala Ile Asp Gln Val Asn Pro Pro Arg
225                 230                 235                 240
Asn Val Thr Val Glu Ile Glu Ser Asn Ser Leu Tyr Ile Gln Trp Glu
                245                 250                 255
Lys Pro Leu Ser Ala Phe Pro Asp His Cys Phe Asn Tyr Glu Leu Lys
            260                 265                 270
Ile Tyr Asn Thr Lys Asn Gly His Ile Gln Lys Glu Lys Leu Ile Ala
        275                 280                 285
Asn Lys Phe Ile Ser Lys Ile Asp Asp Val Ser Thr Tyr Ser Ile Gln
290                 295                 300
Val Arg Ala Ala Val Ser Ser Pro Cys Arg Met Pro Gly Arg Trp Gly
305                 310                 315                 320
Glu Trp Ser Gln Pro Ile Tyr Val Gly Lys Glu Arg Lys Ser Leu Val
                325                 330                 335
Glu Trp His Leu Ile Val Leu Pro Thr Ala Ala Cys Phe Val Leu Leu
            340                 345                 350
Ile Phe Ser Leu Ile Cys Arg Val Cys His Leu Trp Thr Arg Leu Phe
        355                 360                 365
Pro Pro Val Pro Ala Pro Lys Ser Asn Ile Lys Asp Leu Pro Val Val
370                 375                 380
Thr Glu Tyr Glu Lys Pro Ser Asn Glu Thr Lys Ile Glu Val Val His
385                 390                 395                 400
Cys Val Glu Glu Val Gly Phe Glu Val Met Gly Asn Ser Thr Phe
                405                 410                 415
```

(2) INFORMATION FOR SEQ ID NO:6:

(i) SEQUENCE CHARACTERISTICS:
      (A) LENGTH: 398 amino acids
      (B) TYPE: amino acid
      (C) STRANDEDNESS: unknown
      (D) TOPOLOGY: linear (ii) MOLECULE TYPE: peptide (xi) SEQUENCE DESCRIPTION: SEQ ID NO:6:

```
Asp Leu Leu Asn His Lys Lys Phe Leu Leu Pro Pro Val Asn Phe
1               5                   10                  15
Thr Ile Lys Ala Thr Gly Leu Ala Gln Val Leu Leu His Trp Asp Pro
            20                  25                  30
Asn Pro Asp Gln Glu Gln Arg His Val Asp Leu Glu Tyr His Val Lys
        35                  40                  45
Ile Asn Ala Pro Gln Glu Asp Glu Tyr Asp Thr Arg Lys Thr Glu Ser
    50                  55                  60
Lys Cys Val Thr Pro Leu His Glu Gly Phe Ala Ala Ser Val Arg Thr
65                  70                  75                  80
Ile Leu Lys Ser Ser His Thr Thr Leu Ala Ser Ser Trp Val Ser Ala
                85                  90                  95
Glu Leu Lys Ala Pro Pro Gly Ser Pro Gly Thr Ser Val Thr Asn Leu
            100                 105                 110
Thr Cys Thr Thr His Thr Val Val Ser Ser His Thr His Leu Arg Pro
        115                 120                 125
Tyr Gln Val Ser Leu Arg Cys Thr Trp Leu Val Gly Lys Asp Ala Pro
    130                 135                 140
Glu Asp Thr Gln Tyr Phe Leu Tyr Tyr Arg Phe Gly Val Leu Thr Glu
```

```
                145                 150                 155                 160
Lys Cys Gln Glu Tyr Ser Arg Asp Ala Leu Asn Arg Asn Thr Ala Cys
                    165                 170                 175

Trp Phe Pro Arg Thr Phe Ile Asn Ser Lys Gly Phe Glu Gln Leu Ala
                180                 185                 190

Val His Ile Asn Gly Ser Ser Lys Arg Ala Ala Ile Lys Pro Phe Asp
                195                 200                 205

Gln Leu Phe Ser Pro Leu Ala Ile Asp Gln Val Asn Pro Pro Arg Asn
            210                 215                 220

Val Thr Val Glu Ile Glu Ser Asn Ser Leu Tyr Ile Gln Trp Glu Lys
225                 230                 235                 240

Pro Leu Ser Ala Phe Pro Asp His Cys Phe Asn Tyr Glu Leu Lys Ile
                245                 250                 255

Tyr Asn Thr Lys Asn Gly His Ile Gln Lys Glu Lys Leu Ile Ala Asn
                260                 265                 270

Lys Phe Ile Ser Lys Ile Asp Asp Val Ser Thr Tyr Ser Ile Gln Val
                275                 280                 285

Arg Ala Ala Val Ser Ser Pro Cys Arg Met Pro Gly Arg Trp Gly Glu
            290                 295                 300

Trp Ser Gln Pro Ile Tyr Val Gly Lys Glu Arg Lys Ser Leu Val Glu
305                 310                 315                 320

Trp His Leu Ile Val Leu Pro Thr Ala Ala Cys Phe Val Leu Leu Ile
                325                 330                 335

Phe Ser Leu Ile Cys Arg Val Cys His Leu Trp Thr Arg Leu Phe Pro
                340                 345                 350

Pro Val Pro Ala Pro Lys Ser Asn Ile Lys Asp Leu Pro Val Val Thr
            355                 360                 365

Glu Tyr Glu Lys Pro Ser Asn Glu Thr Lys Ile Glu Val Val His Cys
            370                 375                 380

Val Glu Glu Val Gly Phe Glu Val Met Gly Asn Ser Thr Phe
385                 390                 395

(2) INFORMATION FOR SEQ ID NO:7:

(i) SEQUENCE CHARACTERISTICS:
        (A) LENGTH: 332 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:7:

Met Val Pro Val Leu Leu Ile Leu Val Gly Ala Leu Ala Thr Leu Gln
1               5                   10                  15

Ala Asp Leu Leu Asn His Lys Lys Phe Leu Leu Leu Pro Pro Val Asn
                20                  25                  30

Phe Thr Ile Lys Ala Thr Gly Leu Ala Gln Val Leu Leu His Trp Asp
                35                  40                  45

Pro Asn Pro Asp Gln Glu Gln Arg His Val Asp Leu Glu Tyr His Val
            50                  55                  60

Lys Ile Asn Ala Pro Gln Glu Asp Glu Tyr Asp Thr Arg Lys Thr Glu
65                  70                  75                  80

Ser Lys Cys Val Thr Pro Leu His Glu Gly Phe Ala Ala Ser Val Arg
                85                  90                  95

Thr Ile Leu Lys Ser Ser His Thr Thr Leu Ala Ser Ser Trp Val Ser
                100                 105                 110
```

```
Ala Glu Leu Lys Ala Pro Pro Gly Ser Pro Gly Thr Ser Val Thr Asn
            115                 120                 125

Leu Thr Cys Thr Thr His Thr Val Val Ser Ser His Thr His Leu Arg
        130                 135                 140

Pro Tyr Gln Val Ser Leu Arg Cys Thr Trp Leu Val Gly Lys Asp Ala
145                 150                 155                 160

Pro Glu Asp Thr Gln Tyr Phe Leu Tyr Tyr Arg Phe Gly Val Leu Thr
                165                 170                 175

Glu Lys Cys Gln Glu Tyr Ser Arg Asp Ala Leu Asn Arg Asn Thr Ala
            180                 185                 190

Cys Trp Phe Pro Arg Thr Phe Ile Asn Ser Lys Gly Phe Glu Gln Leu
            195                 200                 205

Ala Val His Ile Asn Gly Ser Ser Lys Arg Ala Ala Ile Lys Pro Phe
        210                 215                 220

Asp Gln Leu Phe Ser Pro Leu Ala Ile Asp Gln Val Asn Pro Pro Arg
225                 230                 235                 240

Asn Val Thr Val Glu Ile Glu Ser Asn Ser Leu Tyr Ile Gln Trp Glu
                245                 250                 255

Lys Pro Leu Ser Ala Phe Pro Asp His Cys Phe Asn Tyr Glu Leu Lys
            260                 265                 270

Ile Tyr Asn Thr Lys Asn Gly His Ile Gln Lys Glu Lys Leu Ile Ala
        275                 280                 285

Asn Lys Phe Ile Ser Lys Ile Asp Asp Val Ser Thr Tyr Ser Ile Gln
        290                 295                 300

Val Arg Ala Ala Val Ser Ser Pro Cys Arg Met Pro Gly Arg Trp Gly
305                 310                 315                 320

Glu Trp Ser Gln Pro Ile Tyr Val Glu Thr Phe Glu
                325                 330

(2) INFORMATION FOR SEQ ID NO:8:

(i) SEQUENCE CHARACTERISTICS:
        (A) LENGTH: 315 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:8:

Asp Leu Leu Asn His Lys Lys Phe Leu Leu Pro Pro Val Asn Phe
1               5                   10                  15

Thr Ile Lys Ala Thr Gly Leu Ala Gln Val Leu Leu His Trp Asp Pro
            20                  25                  30

Asn Pro Asp Gln Glu Gln Arg His Val Asp Leu Glu Tyr His Val Lys
            35                  40                  45

Ile Asn Ala Pro Gln Glu Asp Glu Tyr Asp Thr Arg Lys Thr Glu Ser
50                  55                  60

Lys Cys Val Thr Pro Leu His Glu Gly Phe Ala Ala Ser Val Arg Thr
65                  70                  75                  80

Ile Leu Lys Ser Ser His Thr Thr Leu Ala Ser Ser Trp Val Ser Ala
            85                  90                  95

Glu Leu Lys Ala Pro Pro Gly Ser Pro Gly Thr Ser Val Thr Asn Leu
            100                 105                 110

Thr Cys Thr Thr His Thr Val Val Ser Ser His Thr His Leu Arg Pro
            115                 120                 125
```

```
Tyr Gln Val Ser Leu Arg Cys Thr Trp Leu Val Gly Lys Asp Ala Pro
    130                 135                 140

Glu Asp Thr Gln Tyr Phe Leu Tyr Tyr Arg Phe Gly Val Leu Thr Glu
145                 150                 155                 160

Lys Cys Gln Glu Tyr Ser Arg Asp Ala Leu Asn Arg Asn Thr Ala Cys
                165                 170                 175

Trp Phe Pro Arg Thr Phe Ile Asn Ser Lys Gly Phe Glu Gln Leu Ala
            180                 185                 190

Val His Ile Asn Gly Ser Ser Lys Arg Ala Ala Ile Lys Pro Phe Asp
        195                 200                 205

Gln Leu Phe Ser Pro Leu Ala Ile Asp Gln Val Asn Pro Pro Arg Asn
    210                 215                 220

Val Thr Val Glu Ile Glu Ser Asn Ser Leu Tyr Ile Gln Trp Glu Lys
225                 230                 235                 240

Pro Leu Ser Ala Phe Pro Asp His Cys Phe Asn Tyr Glu Leu Lys Ile
                245                 250                 255

Tyr Asn Thr Lys Asn Gly His Ile Gln Lys Glu Lys Leu Ile Ala Asn
            260                 265                 270

Lys Phe Ile Ser Lys Ile Asp Asp Val Ser Thr Tyr Ser Ile Gln Val
        275                 280                 285

Arg Ala Ala Val Ser Ser Pro Cys Arg Met Pro Gly Arg Trp Gly Glu
    290                 295                 300

Trp Ser Gln Pro Ile Tyr Val Glu Thr Phe Glu
305                 310                 315

(2) INFORMATION FOR SEQ ID NO:9:

(i) SEQUENCE CHARACTERISTICS:
        (A) LENGTH: 1260 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

ATGATCATCG TGGCGCATGT ATTACTCATC CTTTTGGGGG CCACTGAGAT ACTGCAAGCT       60

GACTTACTTC CTGATGAAAA GATTTCACTT CTCCCACCTG TCAATTTCAC CATTAAAGTT      120

ACTGGTTTGG CTCAAGTTCT TTTACAATGG AAACCAAATC CTGATCAAGA GCAAAGGAAT      180

GTTAATCTAG AATATCAAGT GAAAATAAAC GCTCCAAAAG AAGATGACTA TGAAACCAGA      240

ATCACTGAAA GCAAATGTGT AACCATCCTC CACAAAGGCT TTTCAGCAAG TGTGCGGACC      300

ATCCTGCAGA ACGACCACTC ACTACTGGCC AGCAGCTGGG CTTCTGCTGA ACTTCATGCC      360

CCACCAGGGT CTCCTGGAAC CTCAGTTGTG AATTTAACTT GCACCACAAA CACTACAGAA      420

GACAATTATT CACGTTTAAG GTCATACCAA GTTTCCCTTC ACTGCACCTG GCTTGTTGGC      480

ACAGATGCCC CTGAGGACAC GCAGTATTTT CTCTACTATA GGTATGGCTC TTGGACTGAA      540

GAATGCCAAG AATACAGCAA AGACACACTG GGGAGAAATA TCGCATGCTG GTTTCCCAGG      600

ACTTTTATCC TCAGCAAAGG GCGTGACTGG CTTGCGGTGC TTGTTAACGG CTCCAGCAAG      660

CACTCTGCTA TCAGGCCCTT TGATCAGCTG TTTGCCCTTC ACGCCATTGA TCAAATAAAT      720

CCTCCACTGA ATGTCACAGC AGAGATTGAA GGAACTCGTC TCTCTATCCA ATGGGAGAAA      780

CCAGTGTCTG CTTTTCCAAT CCATTGCTTT GATTATGAAG TAAAAATACA CAATACAAGG      840

AATGGATATT TGCAGATAGA AAAATTGATG ACCAATGCAT TCATCTCAAT AATTGATGAT      900

CTTTCTAAGT ACGATGTTCA AGTGAGAGCA GCAGTGAGCT CCATGTGCAG AGAGGCAGGG      960
```

```
CTCTGGAGTG AGTGGAGCCA ACCTATTTAT GTGGGAAATG ATGAACACAA GCCCTTGAGA    1020

GAGTGGTTTG TCATTGTGAT TATGGCAACC ATCTGCTTCA TCTTGTTAAT TCTCTCGCTT    1080

ATCTGTAAAA TATGTCATTT ATGGATCAAG TTGTTTCCAC CAATTCCAGC ACCAAAAAGT    1140

AATATCAAAG ATCTCTTTGT AACCACTAAC TATGAGAAAG CTGGGTCCAG TGAGACGGAA    1200

ATTGAAGTCA TCTGTTATAT AGAGAAGCCT GGAGTTGAGA CCCTGGAGGA TTCTGTGTTT    1260
```

(2) INFORMATION FOR SEQ ID NO:10:

(i) SEQUENCE CHARACTERISTICS:
        (A) LENGTH: 2006 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CGGTCCTCGC CATCTTCTGT TGAGTACTGG TCGGAACAAG AGGATCGTCT GTAGACAGGA      60

TATGATCATC GTGGCGCATG TATTACTCAT CCTTTTGGGG GCCACTGAGA TACTGCAAGC     120

TGACTTACTT CCTGATGAAA AGATTTCACT TCTCCCACCT GTCAATTTCA CCATTAAAGT     180

TACTGGTTTG GCTCAAGTTC TTTTACAATG GAAACCAAAT CCTGATCAAG AGCAAAGGAA     240

TGTTAATCTA GAATATCAAG TGAAAATAAA CGCTCCAAAA GAAGATGACT ATGAAACCAG     300

AATCACTGAA AGCAAATGTG TAACCATCCT CCACAAAGGC TTTTCAGCAA GTGTGCGGAC     360

CATCCTGCAG AACGACCACT CACTACTGGC CAGCAGCTGG GCTTCTGCTG AACTTCATGC     420

CCCACCAGGG TCTCCTGGAA CCTCAGTTGT GAATTTAACT TGCACCACAA ACACTACAGA     480

AGACAATTAT TCACGTTTAA GGTCATACCA AGTTTCCCTT CACTGCACCT GGCTTGTTGG     540

CACAGATGCC CCTGAGGACA CGCAGTATTT TCTCTACTAT AGGTATGGCT CTTGGACTGA     600

AGAATGCCAA GAATACAGCA AAGACACACT GGGGAGAAAT ATCGCATGCT GGTTTCCCAG     660

GACTTTTATC CTCAGCAAAG GGCGTGACTG GCTTGCGGTG CTTGTTAACG GCTCCAGCAA     720

GCACTCTGCT ATCAGGCCCT TGATCAGCT GTTTGCCCTT CACGCCATTG ATCAAATAAA     780

TCCTCCACTG AATGTCACAG CAGAGATTGA AGGAACTCGT CTCTCTATCC AATGGGAGAA     840

ACCAGTGTCT GCTTTTCCAA TCCATTGCTT TGATTATGAA GTAAAAATAC ACAATACAAG     900

GAATGGATAT TTGCAGATAG AAAAATTGAT GACCAATGCA TTCATCTCAA TAATTGATGA     960

TCTTTCTAAG TACGATGTTC AAGTGAGAGC AGCAGTGAGC TCCATGTGCA GAGAGGCAGG    1020

GCTCTGGAGT GAGTGGAGCC AACCTATTTA TGTGGGAAAT GATGAACACA AGCCCTTGAG    1080

AGAGTGGTTT GTCATTGTGA TTATGGCAAC CATCTGCTTC ATCTTGTTAA TTCTCTCGCT    1140

TATCTGTAAA ATATGTCATT TATGGATCAA GTTGTTTCCA CCAATTCCAG CACCAAAAAG    1200

TAATATCAAA GATCTCTTTG TAACCACTAA CTATGAGAAA GCTGGGTCCA GTGAGACGGA    1260

AATTGAAGTC ATCTGTTATA TAGAGAAGCC TGGAGTTGAG ACCCTGGAGG ATTCTGTGTT    1320

TTGACTGTCA CTTTGGCATC CTCTGATGAA CTCACACATG CCTCAGTGCC TCAGTGAAAA    1380

GAACAGGGAT GCTGGCTCTT GGCTAAGAGG TGTTCAGAAT TTAGGCAACA CTCAATTTAC    1440

CTGCGAAGCA ATACACCCAG ACACACCAGT CTTGTATCTC TTAAAAGTAT GGATGCTTCA    1500

TCCAAATCGC CTCACCTACA GCAGGGAAGT TGACTCATCC AAGCATTTTG CCATGTTTTT    1560

TCTCCCCATG CCGTACAGGG TAGCACCTCC TCACCTGCCA ATCTTTGCAA TTTGCTTGAC    1620

TCACCTCAGA CTTTTCATTC ACAACAGACA GCTTTTAAGG CTAACGTCCA GCTGTATTTA    1680
```

| | | |
|---|---|---|
| CTTCTGGCTG TGCCCGTTTG GCTGTTTAAG CTGCCAATTG TAGCACTCAG CTACCATCTG | | 1740 |
| AGGAAGAAAG CATTTTGCAT CAGCCTGGAG TGAATCATGA ACTTGGATTC AAGACTGTCT | | 1800 |
| TTTCTATAGC AAGTGAGAGC CACAAATTCC TCACCCCCCT ACATTCTAGA ATGATCTTTT | | 1860 |
| TCTAGGTAGA TTGTGTATGT GTGTGTATGA GAGAGAGAGA GAGAGAGAGA GAGAGAGAGA | | 1920 |
| GAGAAATTAT CTCAAGCTCC AGAGGCCTGA TCCAGGATAC ATCATTTGAA ACCAACTAAT | | 1980 |
| TTAAAAGCAT AATAGAGCTA ATATAT | | 2006 |

(2) INFORMATION FOR SEQ ID NO:11:

(i) SEQUENCE CHARACTERISTICS:
        (A) LENGTH: 1188 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

| | | |
|---|---|---|
| ATGATCATCG TGGCGCATGT ATTACTCATC CTTTTGGGGG CCACTGAGAT ACTGCAAGCT | | 60 |
| GACTTACTTC CTGATGAAAA GATTTCACTT CTCCCACCTG TCAATTTCAC CATTAAAGTT | | 120 |
| ACTGGTTTGG CTCAAGTTCT TTTACAATGG AAACCAAATC CTGATCAAGA GCAAAGGAAT | | 180 |
| GTTAATCTAG AATATCAAGT GAAAATAAAC GCTCCAAAAG AAGATGACTA TGAAACCAGA | | 240 |
| ATCACTGAAA GCAAATGTGT AACCATCCTC CACAAAGGCT TTTCAGCAAG TGTGCGGACC | | 300 |
| ATCCTGCAGA ACGACCACTC ACTACTGGCC AGCAGCTGGG CTTCTGCTGA ACTTCATGCC | | 360 |
| CCACCAGGGT CTCCTGGAAC CTCAATTGTG AATTTAACTT GCACCACAAA CACTACAGAA | | 420 |
| GACAATTATT CACGTTTAAG GTCATACCAA GTTTCCCTTC ACTGCACCTG GCTTGTTGGC | | 480 |
| ACAGATGCCC CTGAGGACAC GCAGTATTTT CTCTACTATA GGTATGGCTC TTGGACTGAA | | 540 |
| GAATGCCAAG AATACAGCAA AGACACACTG GGGAGAAATA TCGCATGCTG GTTTCCCAGG | | 600 |
| ACTTTTATCC TCAGCAAAGG GCGTGACTGG CTTGCGGTGC TTGTTAACGG CTCCAGCAAG | | 660 |
| CACTCTGCTA TCAGGCCCTT TGATCAGCTG TTTGCCCTTC ACGCCATTGA TCAAATAAAT | | 720 |
| CCTCCACTGA ATGTCACAGC AGAGATTGAA GGAACTCGTC TCTCTATCCA ATGGGAGAAA | | 780 |
| CCAGTGTCTG CTTTTCCAAT CCATTGCTTT GATTATGAAG TAAAAATACA CAATACAAGG | | 840 |
| AATGGATATT TGCAGATAGA AAAATTGATG ACCAATGCAT TCATCTCAAT AATTGATGAT | | 900 |
| CTTTCTAAGT ACGATGTTCA AGTGAGAGCA GCAGTGAGCT CCATGTGCAG AGAGGCAGGG | | 960 |
| CTCTGGAGTG AGTGGAGCCA ACCTATTTAT GTGGGAAATG ATGAACACAA GCCCTTGAGA | | 1020 |
| GAGTGGTTTG TCATTGTGAT TATGGCAACC ATCTGCTTCA TCTTGTTAAT TCTCTCGCTT | | 1080 |
| ATCTGTAAAA TATGTCATTT ATGGATCAAG TTGTTTCCAC CAATTCCAGC ACCAAAAAGT | | 1140 |
| AATATCAAAG ATCTCTTTGT AACCACTAAC TATGAGAAAG CTGGAATT | | 1188 |

(2) INFORMATION FOR SEQ ID NO:12:

(i) SEQUENCE CHARACTERISTICS:
        (A) LENGTH: 2024 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

| | | |
|---|---|---|
| TAGATGCTGG GGTTGCAGCC ACGAGCATAG ACACGACAGA CACGGTCCTC GCCATCTTCT | | 60 |

-continued

```
GTTGAGTACT GGTCGGAACA AGAGGATCGT CTGTAGACAG GATATGATCA TCGTGGCGCA        120

TGTATTACTC ATCCTTTTGG GGGCCACTGA GATACTGCAA GCTGACTTAC TTCCTGATGA        180

AAAGATTTCA CTTCTCCCAC CTGTCAATTT CACCATTAAA GTTACTGGTT TGGCTCAAGT        240

TCTTTTACAA TGGAAACCAA ATCCTGATCA AGAGCAAAGG AATGTTAATC TAGAATATCA        300

AGTGAAAATA AACGCTCCAA AGAAGATGA CTATGAAACC AGAATCACTG AAAGCAAATG         360

TGTAACCATC CTCCACAAAG GCTTTTCAGC AAGTGTGCGG ACCATCCTGC AGAACGACCA        420

CTCACTACTG GCCAGCAGCT GGGCTTCTGC TGAACTTCAT GCCCCACCAG GGTCTCCTGG        480

AACCTCAATT GTGAATTTAA CTTGCACCAC AAACACTACA GAAGACAATT ATTCACGTTT        540

AAGGTCATAC CAAGTTTCCC TTCACTGCAC CTGGCTTGTT GGCACAGATG CCCCTGAGGA        600

CACGCAGTAT TTTCTCTACT ATAGGTATGG CTCTTGGACT GAAGAATGCC AAGAATACAG        660

CAAAGACACA CTGGGGAGAA ATATCGCATG CTGGTTTCCC AGGACTTTTA TCCTCAGCAA        720

AGGGCGTGAC TGGCTTGCGG TGCTTGTTAA CGGCTCCAGC AAGCACTCTG CTATCAGGCC        780

CTTTGATCAG CTGTTTGCCC TTCACGCCAT TGATCAAATA AATCCTCCAC TGAATGTCAC        840

AGCAGAGATT GAAGGAACTC GTCTCTCTAT CCAATGGGAA AAACCAGTGT CTGCTTTTCC        900

AATCCATTGC TTTGATTATG AAGTAAAAAT ACACAATACA AGGAATGGAT ATTTGCAGAT        960

AGAAAAATTG ATGACCAATG CATTCATCTC AATAATTGAT GATCTTTCTA AGTACGATGT       1020

TCAAGTGAGA GCAGCAGTGA GCTCCATGTG CAGAGAGGCA GGGCTCTGGA GTGAGTGGAG       1080

CCAACCTATT TATGTGGGAA ATGATGAACA CAAGCCCTTG AGAGAGTGGT TTGTCATTGT       1140

GATTATGGCA ACCATCTGCT TCATCTTGTT AATTCTCTCG CTTATCTGTA AAATATGTCA       1200

TTTATGGATC AAGTTGTTTC CACCAATTCC AGCACCAAAA AGTAATATCA AAGATCTCTT       1260

TGTAACCACT AACTATGAGA AAGCTGGAAT TTAAATTCAA GCATGTTTTA ACTTTTGGTT       1320

TAAGGTACTT GGGTGTACCT GGCAGTGTTG TAAGCTCTTT ACATTAATTA ATTAACTCTC       1380

TAGGTACTGT TATCTTCATT TTATAAACAA GGCAGCTGAA GTTGAGAGAA ATAAGTAACC       1440

TGTCCTAGGT CACACAATTA GGAAATGACA GATCTGGCAG TCTATTTCCA GGCAGTCTAT       1500

TTCCACGAGG TCATGAGTGC GAAAGAGGGA CTAGGGGAAG AATGATTAAC TCCAGGGAGC       1560

TGACTTTTCT AGTGTGCTTA CCTGTTTTGC ATCTCTCAAG GATGTGCCAT GAAGCTGTAG       1620

CCAGGTGGAA TTGTACCACA GCCCTGACAT GAACACCTGA TGGCAGCTGC TGGGTTGGAG       1680

CCTAGACAAA AACATGAAGA ACCATGGCTG CTGCCTGAGC CCATCGTGCT GTAATTATAG       1740

AAAACCTTCT AAGGGAAGAA TATGCTGATA TTTTTCAGAT AAGTACCCCT TTTATAAAAA       1800

TCCTCCAAGT TAGCCCTCGA TTTTCCATGT AAGGAAACAG AGGCTTTGAG ATAATGTCTG       1860

TCTCCTAAGG GACAAAGCCA GGACTTGATC CTGTCTTAAA AATGCAAAAT GTAGTACTTC       1920

TTCCATCAAA GGTAGACATG CACTAAGGGA CAGGTTTTGG CTTGGTATCA GAATACATTT       1980

TTAAAAGCTG TGTAAGAATT GAACGGGCTG TACTAGGGGG TATA                       2024
```

(2) INFORMATION FOR SEQ ID NO:13:

(i) SEQUENCE CHARACTERISTICS:
        (A) LENGTH: 420 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:13:

Met Ile Ile Val Ala His Val Leu Leu Ile Leu Leu Gly Ala Thr Glu

```
      1               5                   10                  15
Ile Leu Gln Ala Asp Leu Leu Pro Asp Glu Lys Ile Ser Leu Leu Pro
                20                  25                  30

Pro Val Asn Phe Thr Ile Lys Val Thr Gly Leu Ala Gln Val Leu Leu
                35                  40                  45

Gln Trp Lys Pro Asn Pro Asp Gln Glu Gln Arg Asn Val Asn Leu Glu
                50                  55                  60

Tyr Gln Val Lys Ile Asn Ala Pro Lys Glu Asp Asp Tyr Glu Thr Arg
65                  70                  75                  80

Ile Thr Glu Ser Lys Cys Val Thr Ile Leu His Lys Gly Phe Ser Ala
                85                  90                  95

Ser Val Arg Thr Ile Leu Gln Asn Asp His Ser Leu Leu Ala Ser Ser
                100                 105                 110

Trp Ala Ser Ala Glu Leu His Ala Pro Pro Gly Ser Pro Gly Thr Ser
                115                 120                 125

Val Val Asn Leu Thr Cys Thr Thr Asn Thr Thr Glu Asp Asn Tyr Ser
                130                 135                 140

Arg Leu Arg Ser Tyr Gln Val Ser Leu His Cys Thr Trp Leu Val Gly
145                 150                 155                 160

Thr Asp Ala Pro Glu Asp Thr Gln Tyr Phe Leu Tyr Tyr Arg Tyr Gly
                165                 170                 175

Ser Trp Thr Glu Glu Cys Gln Glu Tyr Ser Lys Asp Thr Leu Gly Arg
                180                 185                 190

Asn Ile Ala Cys Trp Phe Pro Arg Thr Phe Ile Leu Ser Lys Gly Arg
                195                 200                 205

Asp Trp Leu Ala Val Leu Val Asn Gly Ser Ser Lys His Ser Ala Ile
                210                 215                 220

Arg Pro Phe Asp Gln Leu Phe Ala Leu His Ala Ile Asp Gln Ile Asn
225                 230                 235                 240

Pro Pro Leu Asn Val Thr Ala Glu Ile Glu Gly Thr Arg Leu Ser Ile
                245                 250                 255

Gln Trp Glu Lys Pro Val Ser Ala Phe Pro Ile His Cys Phe Asp Tyr
                260                 265                 270

Glu Val Lys Ile His Asn Thr Arg Asn Gly Tyr Leu Gln Ile Glu Lys
                275                 280                 285

Leu Met Thr Asn Ala Phe Ile Ser Ile Ile Asp Asp Leu Ser Lys Tyr
                290                 295                 300

Asp Val Gln Val Arg Ala Ala Val Ser Ser Met Cys Arg Glu Ala Gly
305                 310                 315                 320

Leu Trp Ser Glu Trp Ser Gln Pro Ile Tyr Val Gly Asn Asp Glu His
                325                 330                 335

Lys Pro Leu Arg Glu Trp Phe Val Ile Val Ile Met Ala Thr Ile Cys
                340                 345                 350

Phe Ile Leu Leu Ile Leu Ser Leu Ile Cys Lys Ile Cys His Leu Trp
                355                 360                 365

Ile Lys Leu Phe Pro Pro Ile Pro Ala Pro Lys Ser Asn Ile Lys Asp
                370                 375                 380

Leu Phe Val Thr Thr Asn Tyr Glu Lys Ala Gly Ser Ser Glu Thr Glu
385                 390                 395                 400

Ile Glu Val Ile Cys Tyr Ile Glu Lys Pro Gly Val Glu Thr Leu Glu
                405                 410                 415

Asp Ser Val Phe
                420
```

(2) INFORMATION FOR SEQ ID NO:14:

(i) SEQUENCE CHARACTERISTICS:
    (A) LENGTH: 396 amino acids
    (B) TYPE: amino acid
    (C) STRANDEDNESS: unknown
    (D) TOPOLOGY: linear (ii) MOLECULE TYPE: peptide (xi) SEQUENCE DESCRIPTION: SEQ ID NO:14:

```
Met Ile Ile Val Ala His Val Leu Leu Ile Leu Leu Gly Ala Thr Glu
1               5                   10                  15

Ile Leu Gln Ala Asp Leu Leu Pro Asp Glu Lys Ile Ser Leu Leu Pro
            20                  25                  30

Pro Val Asn Phe Thr Ile Lys Val Thr Gly Leu Ala Gln Val Leu Leu
        35                  40                  45

Gln Trp Lys Pro Asn Pro Asp Gln Glu Gln Arg Asn Val Asn Leu Glu
50                  55                  60

Tyr Gln Val Lys Ile Asn Ala Pro Lys Glu Asp Asp Tyr Glu Thr Arg
65                  70                  75                  80

Ile Thr Glu Ser Lys Cys Val Thr Ile Leu His Lys Gly Phe Ser Ala
                85                  90                  95

Ser Val Arg Thr Ile Leu Gln Asn Asp His Ser Leu Leu Ala Ser Ser
            100                 105                 110

Trp Ala Ser Ala Glu Leu His Ala Pro Pro Gly Ser Pro Gly Thr Ser
        115                 120                 125

Ile Val Asn Leu Thr Cys Thr Thr Asn Thr Thr Glu Asp Asn Tyr Ser
130                 135                 140

Arg Leu Arg Ser Tyr Gln Val Ser Leu His Cys Thr Trp Leu Val Gly
145                 150                 155                 160

Thr Asp Ala Pro Glu Asp Thr Gln Tyr Phe Leu Tyr Tyr Arg Tyr Gly
                165                 170                 175

Ser Trp Thr Glu Glu Cys Gln Glu Tyr Ser Lys Asp Thr Leu Gly Arg
            180                 185                 190

Asn Ile Ala Cys Trp Phe Pro Arg Thr Phe Ile Leu Ser Lys Gly Arg
        195                 200                 205

Asp Trp Leu Ala Val Leu Val Asn Gly Ser Ser Lys His Ser Ala Ile
210                 215                 220

Arg Pro Phe Asp Gln Leu Phe Ala Leu His Ala Ile Asp Gln Ile Asn
225                 230                 235                 240

Pro Pro Leu Asn Val Thr Ala Glu Ile Glu Gly Thr Arg Leu Ser Ile
                245                 250                 255

Gln Trp Glu Lys Pro Val Ser Ala Phe Pro Ile His Cys Phe Asp Tyr
            260                 265                 270

Glu Val Lys Ile His Asn Thr Arg Asn Gly Tyr Leu Gln Ile Glu Lys
        275                 280                 285

Leu Met Thr Asn Ala Phe Ile Ser Ile Ile Asp Asp Leu Ser Lys Tyr
290                 295                 300

Asp Val Gln Val Arg Ala Ala Val Ser Ser Met Cys Arg Glu Ala Gly
305                 310                 315                 320

Leu Trp Ser Glu Trp Ser Gln Pro Ile Tyr Val Gly Asn Asp Glu His
                325                 330                 335

Lys Pro Leu Arg Glu Trp Phe Val Ile Val Ile Met Ala Thr Ile Cys
            340                 345                 350

Phe Ile Leu Leu Ile Leu Ser Leu Ile Cys Lys Ile Cys His Leu Trp
```

```
                       355                 360                     365
Ile Lys Leu Phe Pro Pro Ile Pro Ala Pro Lys Ser Asn Ile Lys Asp
    370                     375                 380
Leu Phe Val Thr Thr Asn Tyr Glu Lys Ala Gly Ile
385                     390                 395
```

(2) INFORMATION FOR SEQ ID NO:15:

(i) SEQUENCE CHARACTERISTICS:
        (A) LENGTH: 1808 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 303..1547

(xi) SEQUENCE DESCRIPTION: SEQ ID NO:15:

```
GAAATAATTG GTAAACACAG AAAATGTTTC AATAGAAAAA AGAGGAAACA GAACACTGTG      60

TAGCCCTGTT ATCAGCAGAG ACAGAGCTAA CGCTGGGGAT ACCAAACTAG AAGAAGCTCA    120

CTGGACAGGT CCCGGTATGC AGTTCTATTT TTGTTGATGG CTCTGTATCT AATGTGTTCA    180

TTTGTACCAA GGATCTAACC AGGGTCTTCC AGAGTCTGAG CAAGCTTCTC CCACTGAGCT    240

ACATCACAGC CCCCTGTTTA TTGGAAGAAG AAATACTTAC ACCTTTCCAG TATTCGGCTA    300

CC ATG GTG CCT GTG TTA CTA ATT CTT GTG GGA GCT TTG GCA ACA CTG      347
   Met Val Pro Val Leu Leu Ile Leu Val Gly Ala Leu Ala Thr Leu
    1               5                  10                  15

CAA GCT GAC TTA CTT AAT CAC AAA AAG TTT TTA CTT CTA CCA CCT GTC      395
Gln Ala Asp Leu Leu Asn His Lys Lys Phe Leu Leu Leu Pro Pro Val
                 20                  25                  30

AAT TTT ACC ATT AAA GCC ACT GGA TTA GCT CAA GTT CTT TTA CAC TGG      443
Asn Phe Thr Ile Lys Ala Thr Gly Leu Ala Gln Val Leu Leu His Trp
             35                  40                  45

GAC CCA AAT CCT GAC CAA GAG CAA AGG CAT GTT GAT CTA GAG TAT CAC      491
Asp Pro Asn Pro Asp Gln Glu Gln Arg His Val Asp Leu Glu Tyr His
         50                  55                  60

GTG AAA ATA AAT GCC CCA CAA GAA GAC GAA TAT GAT ACC AGA AAG ACT      539
Val Lys Ile Asn Ala Pro Gln Glu Asp Glu Tyr Asp Thr Arg Lys Thr
 65                  70                  75

GAA AGC AAA TGT GTG ACC CCC CTT CAT GAA GGC TTT GCA GCT AGC GTG      587
Glu Ser Lys Cys Val Thr Pro Leu His Glu Gly Phe Ala Ala Ser Val
 80                  85                  90                  95

AGG ACC ATT CTG AAG AGC AGC CAT ACA ACT CTG GCC AGC AGT TGG GTT      635
Arg Thr Ile Leu Lys Ser Ser His Thr Thr Leu Ala Ser Ser Trp Val
                100                 105                 110

TCT GCT GAA CTC AAA GCT CCA CCA GGA TCT CCT GGA ACC TCG GTT ACG      683
Ser Ala Glu Leu Lys Ala Pro Pro Gly Ser Pro Gly Thr Ser Val Thr
            115                 120                 125

AAT TTA ACT TGT ACC ACA CAC ACT GTT GTA AGT AGC CAC ACC CAC TTA      731
Asn Leu Thr Cys Thr Thr His Thr Val Val Ser Ser His Thr His Leu
        130                 135                 140

AGG CCA TAC CAA GTG TCC CTT CGT TGC ACC TGG CTT GTT GGG AAG GAT      779
Arg Pro Tyr Gln Val Ser Leu Arg Cys Thr Trp Leu Val Gly Lys Asp
    145                 150                 155

GCC CCT GAG GAC ACA CAG TAT TTC CTA TAC TAC AGG TTT GGT GTT TTG      827
Ala Pro Glu Asp Thr Gln Tyr Phe Leu Tyr Tyr Arg Phe Gly Val Leu
160                 165                 170                 175

ACT GAA AAA TGC CAA GAA TAC AGC AGA GAT GCA CTG AAC AGA AAT ACT      875
```

```
          Thr Glu Lys Cys Gln Glu Tyr Ser Arg Asp Ala Leu Asn Arg Asn Thr
                          180                 185                 190

GCA TGC TGG TTT CCC AGG ACA TTT ATC AAC AGC AAA GGG TTT GAA CAG                923
Ala Cys Trp Phe Pro Arg Thr Phe Ile Asn Ser Lys Gly Phe Glu Gln
            195                 200                 205

CTT GCT GTG CAC ATT AAT GGC TCA AGC AAG CGT GCT GCA ATC AAG CCC                971
Leu Ala Val His Ile Asn Gly Ser Ser Lys Arg Ala Ala Ile Lys Pro
            210                 215                 220

TTT GAT CAG CTG TTC AGT CCA CTT GCC ATT GAC CAA GTG AAT CCT CCA               1019
Phe Asp Gln Leu Phe Ser Pro Leu Ala Ile Asp Gln Val Asn Pro Pro
225                 230                 235

AGG AAT GTC ACA GTG GAA ATT GAA AGC AAT TCT CTC TAT ATA CAG TGG               1067
Arg Asn Val Thr Val Glu Ile Glu Ser Asn Ser Leu Tyr Ile Gln Trp
240                 245                 250                 255

GAG AAA CCA CTT TCT GCC TTT CCA GAT CAT TGC TTT AAC TAT GAG CTG               1115
Glu Lys Pro Leu Ser Ala Phe Pro Asp His Cys Phe Asn Tyr Glu Leu
                260                 265                 270

AAA ATT TAC AAC ACA AAA AAT GGT CAC ATT CAG AAG GAA AAA CTG ATC               1163
Lys Ile Tyr Asn Thr Lys Asn Gly His Ile Gln Lys Glu Lys Leu Ile
                275                 280                 285

GCC AAT AAG TTC ATC TCA AAA ATT GAT GAT GTT TCT ACA TAT TCC ATT               1211
Ala Asn Lys Phe Ile Ser Lys Ile Asp Asp Val Ser Thr Tyr Ser Ile
            290                 295                 300

CAA GTG AGA GCA GCT GTG AGC TCA CCT TGC AGA ATG CCA GGA AGG TGG               1259
Gln Val Arg Ala Ala Val Ser Ser Pro Cys Arg Met Pro Gly Arg Trp
            305                 310                 315

GGC GAG TGG AGT CAA CCT ATT TAT GTG GGA AAG GAA AGG AAG TCC TTG               1307
Gly Glu Trp Ser Gln Pro Ile Tyr Val Gly Lys Glu Arg Lys Ser Leu
320                 325                 330                 335

GTA GAA TGG CAT CTC ATT GTG CTC CCA ACA GCT GCC TGC TTC GTC TTG               1355
Val Glu Trp His Leu Ile Val Leu Pro Thr Ala Ala Cys Phe Val Leu
                340                 345                 350

TTA ATC TTC TCA CTC ATC TGC AGA GTG TGT CAT TTA TGG ACC AGG TTG               1403
Leu Ile Phe Ser Leu Ile Cys Arg Val Cys His Leu Trp Thr Arg Leu
                355                 360                 365

TTT CCA CCG GTT CCG GCC CCA AAG AGT AAC ATC AAA GAT CTC CCT GTG              1451
Phe Pro Pro Val Pro Ala Pro Lys Ser Asn Ile Lys Asp Leu Pro Val
            370                 375                 380

GTT ACT GAA TAT GAG AAA CCT TCG AAT GAA ACC AAA ATT GAA GTT GTA               1499
Val Thr Glu Tyr Glu Lys Pro Ser Asn Glu Thr Lys Ile Glu Val Val
385                 390                 395

CAT TGT GTG GAA GAG GTT GGA TTT GAA GTC ATG GGA AAT TCC ACG TTT               1547
His Cys Val Glu Glu Val Gly Phe Glu Val Met Gly Asn Ser Thr Phe
400                 405                 410                 415

TGATGGCATT TGCCATTCT  GAAATGAACT  CATACAGGAC  TCCGTGATAA  AGCAAGGAC           1607

TGCTATTTCT TGGCAAGGAG GTATTTCAAA TGAACACTCA GAGCCAGGCG GTGGTAGAGC             1667

TCGCCTTTAA TACCAGCACC TGGGATGCAC AGACGGGAGG ATTTCTGAGT TCGAGGCCAG             1727

CTTGGTCTAT AAAGTGAGTT CCAGGACAGC CAGAGCTACA CAGAGAAACC CTGTCTCGAA             1787

AAAACAAACA AACAAACAAA C                                                      1808

(2) INFORMATION FOR SEQ ID NO:16:

(i) SEQUENCE CHARACTERISTICS:
        (A) LENGTH: 1355 base pairs
        (B) TYPE: nucleic acid
        (C) STRANDEDNESS: single
        (D) TOPOLOGY: linear (ii) MOLECULE TYPE: cDNA
```

(ix) FEATURE:
    (A) NAME/KEY: CDS
    (B) LOCATION: 13..1008

(xi) SEQUENCE DESCRIPTION: SEQ ID NO:16:

```
TATTCGGCTA CC ATG GTG CCT GTG TTA CTA ATT CTT GTG GGA GCT TTG         48
              Met Val Pro Val Leu Leu Ile Leu Val Gly Ala Leu
                1               5                  10

GCA ACA CTG CAA GCT GAC TTA CTT AAT CAC AAA AAG TTT TTA CTT CTA      96
Ala Thr Leu Gln Ala Asp Leu Leu Asn His Lys Lys Phe Leu Leu Leu
             15                  20                  25

CCA CCT GTC AAT TTT ACC ATT AAA GCC ACT GGA TTA GCT CAA GTT CTT     144
Pro Pro Val Asn Phe Thr Ile Lys Ala Thr Gly Leu Ala Gln Val Leu
 30                  35                  40

TTA CAC TGG GAC CCA AAT CCT GAC CAA GAG CAA AGG CAT GTT GAT CTA     192
Leu His Trp Asp Pro Asn Pro Asp Gln Glu Gln Arg His Val Asp Leu
 45                  50                  55                  60

GAG TAT CAC GTG AAA ATA AAT GCC CCA CAA GAA GAC GAA TAT GAT ACC     240
Glu Tyr His Val Lys Ile Asn Ala Pro Gln Glu Asp Glu Tyr Asp Thr
                 65                  70                  75

AGA AAG ACT GAA AGC AAA TGT GTG ACC CCC CTT CAT GAA GGC TTT GCA     288
Arg Lys Thr Glu Ser Lys Cys Val Thr Pro Leu His Glu Gly Phe Ala
             80                  85                  90

GCT AGC GTG AGG ACC ATT CTG AAG AGC AGC CAT ACA ACT CTG GCC AGC     336
Ala Ser Val Arg Thr Ile Leu Lys Ser Ser His Thr Thr Leu Ala Ser
         95                 100                 105

AGT TGG GTT TCT GCT GAA CTC AAA GCT CCA CCA GGA TCT CCT GGA ACC     384
Ser Trp Val Ser Ala Glu Leu Lys Ala Pro Pro Gly Ser Pro Gly Thr
    110                 115                 120

TCG GTT ACG AAT TTA ACT TGT ACC ACA CAC ACT GTT GTA AGT AGC CAC     432
Ser Val Thr Asn Leu Thr Cys Thr Thr His Thr Val Val Ser Ser His
125                 130                 135                 140

ACC CAC TTA AGG CCA TAC CAA GTG TCC CTT CGT TGC ACC TGG CTT GTT     480
Thr His Leu Arg Pro Tyr Gln Val Ser Leu Arg Cys Thr Trp Leu Val
                145                 150                 155

GGG AAG GAT GCC CCT GAG GAC ACA CAG TAT TTC CTA TAC TAC AGG TTT     528
Gly Lys Asp Ala Pro Glu Asp Thr Gln Tyr Phe Leu Tyr Tyr Arg Phe
            160                 165                 170

GGT GTT TTG ACT GAA AAA TGC CAA GAA TAC AGC AGA GAT GCA CTG AAC     576
Gly Val Leu Thr Glu Lys Cys Gln Glu Tyr Ser Arg Asp Ala Leu Asn
        175                 180                 185

AGA AAT ACT GCA TGC TGG TTT CCC AGG ACA TTT ATC AAC AGC AAA GGG     624
Arg Asn Thr Ala Cys Trp Phe Pro Arg Thr Phe Ile Asn Ser Lys Gly
    190                 195                 200

TTT GAA CAG CTT GCT GTG CAC ATT AAT GGC TCA AGC AAG CGT GCT GCA     672
Phe Glu Gln Leu Ala Val His Ile Asn Gly Ser Ser Lys Arg Ala Ala
205                 210                 215                 220

ATC AAG CCC TTT GAT CAG CTG TTC AGT CCA CTT GCC ATT GAC CAA GTG     720
Ile Lys Pro Phe Asp Gln Leu Phe Ser Pro Leu Ala Ile Asp Gln Val
                225                 230                 235

AAT CCT CCA AGG AAT GTC ACA GTG GAA ATT GAA AGC AAT TCT CTC TAT     768
Asn Pro Pro Arg Asn Val Thr Val Glu Ile Glu Ser Asn Ser Leu Tyr
            240                 245                 250

ATA CAG TGG GAG AAA CCA CTT TCT GCC TTT CCA GAT CAT TGC TTT AAC     816
Ile Gln Trp Glu Lys Pro Leu Ser Ala Phe Pro Asp His Cys Phe Asn
        255                 260                 265

TAT GAG CTG AAA ATT TAC AAC ACA AAA AAT GGT CAC ATT CAG AAG GAA     864
Tyr Glu Leu Lys Ile Tyr Asn Thr Lys Asn Gly His Ile Gln Lys Glu
    270                 275                 280

AAA CTG ATC GCC AAT AAG TTC ATC TCA AAA ATT GAT GAT GTT TCT ACA     912
Lys Leu Ile Ala Asn Lys Phe Ile Ser Lys Ile Asp Asp Val Ser Thr
```

```
              285                 290                 295                 300
TAT TCC ATT CAA GTG AGA GCA GCT GTG AGC TCA CCT TGC AGA ATG CCA                960
Tyr Ser Ile Gln Val Arg Ala Ala Val Ser Ser Pro Cys Arg Met Pro
                            305                 310                 315

GGA AGG TGG GGC GAG TGG AGT CAA CCT ATT TAT GTG GAA ACC TTC GAA               1008
Gly Arg Trp Gly Glu Trp Ser Gln Pro Ile Tyr Val Glu Thr Phe Glu
                    320                 325                 330

TGAAACCAAA ATTGAAGTTG TACATTGTGT GGAAGAGGTT GGATTTGAAG TCATGGGAAA             1068

TTCCACGTTT TGATGGCATT TTGCCATTCT GAAATGAACT CATACAGGAC TCCGTGATAA             1128

GAGCAAGGAC TGCTATTTCT TGGCAAGGAG GTATTTCAAA TGAACACTCA GAGCCAGGCG             1188

GTGGTAGAGC TCGCCTTTAA TACCAGCACC TGGGATGCAC AGACGGGAGG ATTTCTGAGT             1248

TCGAGGCCAG CTTGGTCTAT AAAGTGAGTT CCAGGACAGC CAGAGCTACA CAGAGAAACC             1308

CTGTCTCGAA AAACAAACA AACAAACAAA CAAACAAAAA TGAACAC                            1355

(2) INFORMATION FOR SEQ ID NO:17:

(i) SEQUENCE CHARACTERISTICS:
        (A) LENGTH: 2006 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 62..1324

(xi) SEQUENCE DESCRIPTION: SEQ ID NO:17:

CGGTCCTCGC CATCTTCTGT TGAGTACTGG TCGGAACAAG AGGATCGTCT GTAGACAGGA               60

T ATG ATC ATC GTG GCG CAT GTA TTA CTC ATC CTT TTG GGG GCC ACT                  106
  Met Ile Ile Val Ala His Val Leu Leu Ile Leu Leu Gly Ala Thr
  1               5                   10                  15

GAG ATA CTG CAA GCT GAC TTA CTT CCT GAT GAA AAG ATT TCA CTT CTC                154
Glu Ile Leu Gln Ala Asp Leu Leu Pro Asp Glu Lys Ile Ser Leu Leu
                20                  25                  30

CCA CCT GTC AAT TTC ACC ATT AAA GTT ACT GGT TTG GCT CAA GTT CTT                202
Pro Pro Val Asn Phe Thr Ile Lys Val Thr Gly Leu Ala Gln Val Leu
            35                  40                  45

TTA CAA TGG AAA CCA AAT CCT GAT CAA GAG CAA AGG AAT GTT AAT CTA                250
Leu Gln Trp Lys Pro Asn Pro Asp Gln Glu Gln Arg Asn Val Asn Leu
        50                  55                  60

GAA TAT CAA GTG AAA ATA AAC GCT CCA AAA GAA GAT GAC TAT GAA ACC                298
Glu Tyr Gln Val Lys Ile Asn Ala Pro Lys Glu Asp Asp Tyr Glu Thr
    65                  70                  75

AGA ATC ACT GAA AGC AAA TGT GTA ACC ATC CTC CAC AAA GGC TTT TCA                346
Arg Ile Thr Glu Ser Lys Cys Val Thr Ile Leu His Lys Gly Phe Ser
80                  85                  90                  95

GCA AGT GTG CGG ACC ATC CTG CAG AAC GAC CAC TCA CTA CTG GCC AGC                394
Ala Ser Val Arg Thr Ile Leu Gln Asn Asp His Ser Leu Leu Ala Ser
                100                 105                 110

AGC TGG GCT TCT GCT GAA CTT CAT GCC CCA CCA GGG TCT CCT GGA ACC                442
Ser Trp Ala Ser Ala Glu Leu His Ala Pro Pro Gly Ser Pro Gly Thr
            115                 120                 125

TCA GTT GTG AAT TTA ACT TGC ACC ACA AAC ACT ACA GAA GAC AAT TAT                490
Ser Val Val Asn Leu Thr Cys Thr Thr Asn Thr Thr Glu Asp Asn Tyr
        130                 135                 140

TCA CGT TTA AGG TCA TAC CAA GTT TCC CTT CAC TGC ACC TGG CTT GTT                538
Ser Arg Leu Arg Ser Tyr Gln Val Ser Leu His Cys Thr Trp Leu Val
    145                 150                 155
```

```
GGC ACA GAT GCC CCT GAG GAC ACG CAG TAT TTT CTC TAC TAT AGG TAT      586
Gly Thr Asp Ala Pro Glu Asp Thr Gln Tyr Phe Leu Tyr Tyr Arg Tyr
160                 165                 170                 175

GGC TCT TGG ACT GAA GAA TGC CAA GAA TAC AGC AAA GAC ACA CTG GGG      634
Gly Ser Trp Thr Glu Glu Cys Gln Glu Tyr Ser Lys Asp Thr Leu Gly
                180                 185                 190

AGA AAT ATC GCA TGC TGG TTT CCC AGG ACT TTT ATC CTC AGC AAA GGG      682
Arg Asn Ile Ala Cys Trp Phe Pro Arg Thr Phe Ile Leu Ser Lys Gly
            195                 200                 205

CGT GAC TGG CTT GCG GTG CTT GTT AAC GGC TCC AGC AAG CAC TCT GCT      730
Arg Asp Trp Leu Ala Val Leu Val Asn Gly Ser Ser Lys His Ser Ala
        210                 215                 220

ATC AGG CCC TTT GAT CAG CTG TTT GCC CTT CAC GCC ATT GAT CAA ATA      778
Ile Arg Pro Phe Asp Gln Leu Phe Ala Leu His Ala Ile Asp Gln Ile
    225                 230                 235

AAT CCT CCA CTG AAT GTC ACA GCA GAG ATT GAA GGA ACT CGT CTC TCT      826
Asn Pro Pro Leu Asn Val Thr Ala Glu Ile Glu Gly Thr Arg Leu Ser
240                 245                 250                 255

ATC CAA TGG GAG AAA CCA GTG TCT GCT TTT CCA ATC CAT TGC TTT GAT      874
Ile Gln Trp Glu Lys Pro Val Ser Ala Phe Pro Ile His Cys Phe Asp
                260                 265                 270

TAT GAA GTA AAA ATA CAC AAT ACA AGG AAT GGA TAT TTG CAG ATA GAA      922
Tyr Glu Val Lys Ile His Asn Thr Arg Asn Gly Tyr Leu Gln Ile Glu
            275                 280                 285

AAA TTG ATG ACC AAT GCA TTC ATC TCA ATA ATT GAT GAT CTT TCT AAG      970
Lys Leu Met Thr Asn Ala Phe Ile Ser Ile Ile Asp Asp Leu Ser Lys
        290                 295                 300

TAC GAT GTT CAA GTG AGA GCA GCA GTG AGC TCC ATG TGC AGA GAG GCA     1018
Tyr Asp Val Gln Val Arg Ala Ala Val Ser Ser Met Cys Arg Glu Ala
    305                 310                 315

GGG CTC TGG AGT GAG TGG AGC CAA CCT ATT TAT GTG GGA AAT GAT GAA     1066
Gly Leu Trp Ser Glu Trp Ser Gln Pro Ile Tyr Val Gly Asn Asp Glu
320                 325                 330                 335

CAC AAG CCC TTG AGA GAG TGG TTT GTC ATT GTG ATT ATG GCA ACC ATC     1114
His Lys Pro Leu Arg Glu Trp Phe Val Ile Val Ile Met Ala Thr Ile
                340                 345                 350

TGC TTC ATC TTG TTA ATT CTC TCG CTT ATC TGT AAA ATA TGT CAT TTA     1162
Cys Phe Ile Leu Leu Ile Leu Ser Leu Ile Cys Lys Ile Cys His Leu
            355                 360                 365

TGG ATC AAG TTG TTT CCA CCA ATT CCA GCA CCA AAA AGT AAT ATC AAA     1210
Trp Ile Lys Leu Phe Pro Pro Ile Pro Ala Pro Lys Ser Asn Ile Lys
        370                 375                 380

GAT CTC TTT GTA ACC ACT AAC TAT GAG AAA GCT GGG TCC AGT GAG ACG     1258
Asp Leu Phe Val Thr Thr Asn Tyr Glu Lys Ala Gly Ser Ser Glu Thr
    385                 390                 395

GAA ATT GAA GTC ATC TGT TAT ATA GAG AAG CCT GGA GTT GAG ACC CTG     1306
Glu Ile Glu Val Ile Cys Tyr Ile Glu Lys Pro Gly Val Glu Thr Leu
400                 405                 410                 415

GAG GAT TCT GTG TTT TGACTGTCAC TTTGGCATCC TCTGATGAAC TCACACATGC     1361
Glu Asp Ser Val Phe
                420

CTCAGTGCCT CAGTGAAAAG AACAGGGATG CTGGCTCTTG GCTAAGAGGT GTTCAGAATT   1421

TAGGCAACAC TCAATTTACC TGCGAAGCAA TACACCCAGA CACACCAGTC TTGTATCTCT   1481

TAAAAGTATG GATGCTTCAT CCAAATCGCC TCACCTACAG CAGGGAAGTT GACTCATCCA   1541

AGCATTTTGC CATGTTTTTT CTCCCCATGC CGTACAGGGT AGCACCTCCT CACCTGCCAA   1601

TCTTTGCAAT TTGCTTGACT CACCTCAGAC TTTTCATTCA CAACAGACAG CTTTTAAGGC   1661

TAACGTCCAG CTGTATTTAC TTCTGGCTGT GCCCGTTTGG CTGTTTAAGC TGCCAATTGT   1721
```

```
AGCACTCAGC TACCATCTGA GGAAGAAAGC ATTTTGCATC AGCCTGGAGT GAATCATGAA    1781

CTTGGATTCA AGACTGTCTT TTCTATAGCA AGTGAGAGCC ACAAATTCCT CACCCCCCTA    1841

CATTCTAGAA TGATCTTTTT CTAGGTAGAT TGTGTATGTG TGTGTATGAG AGAGAGAGAG    1901

AGAGAGAGAG AGAGAGAGAG AGAAATTATC TCAAGCTCCA GAGGCCTGAT CCAGGATACA    1961

TCATTTGAAA CCAACTAATT TAAAAGCATA ATAGAGCTAA TATAT                    2006

(2) INFORMATION FOR SEQ ID NO:18:

(i) SEQUENCE CHARACTERISTICS:
        (A) LENGTH: 2024 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 104..1291

(xi) SEQUENCE DESCRIPTION: SEQ ID NO:18:

TAGATGCTGG GGTTGCAGCC ACGAGCATAG ACACGACAGA CACGGTCCTC GCCATCTTCT    60

GTTGAGTACT GGTCGGAACA AGAGGATCGT CTGTAGACAG GAT ATG ATC ATC GTG     115
                                                Met Ile Ile Val
                                                 1

GCG CAT GTA TTA CTC ATC CTT TTG GGG GCC ACT GAG ATA CTG CAA GCT     163
Ala His Val Leu Leu Ile Leu Leu Gly Ala Thr Glu Ile Leu Gln Ala
 5                  10                  15                  20

GAC TTA CTT CCT GAT GAA AAG ATT TCA CTT CTC CCA CCT GTC AAT TTC     211
Asp Leu Leu Pro Asp Glu Lys Ile Ser Leu Leu Pro Pro Val Asn Phe
                25                  30                  35

ACC ATT AAA GTT ACT GGT TTG GCT CAA GTT CTT TTA CAA TGG AAA CCA     259
Thr Ile Lys Val Thr Gly Leu Ala Gln Val Leu Leu Gln Trp Lys Pro
            40                  45                  50

AAT CCT GAT CAA GAG CAA AGG AAT GTT AAT CTA GAA TAT CAA GTG AAA     307
Asn Pro Asp Gln Glu Gln Arg Asn Val Asn Leu Glu Tyr Gln Val Lys
        55                  60                  65

ATA AAC GCT CCA AAA GAA GAT GAC TAT GAA ACC AGA ATC ACT GAA AGC     355
Ile Asn Ala Pro Lys Glu Asp Asp Tyr Glu Thr Arg Ile Thr Glu Ser
 70                  75                  80

AAA TGT GTA ACC ATC CTC CAC AAA GGC TTT TCA GCA AGT GTG CGG ACC     403
Lys Cys Val Thr Ile Leu His Lys Gly Phe Ser Ala Ser Val Arg Thr
85                  90                  95                 100

ATC CTG CAG AAC GAC CAC TCA CTA CTG GCC AGC AGC TGG GCT TCT GCT     451
Ile Leu Gln Asn Asp His Ser Leu Leu Ala Ser Ser Trp Ala Ser Ala
                105                 110                 115

GAA CTT CAT GCC CCA CCA GGG TCT CCT GGA ACC TCA ATT GTG AAT TTA     499
Glu Leu His Ala Pro Pro Gly Ser Pro Gly Thr Ser Ile Val Asn Leu
            120                 125                 130

ACT TGC ACC ACA AAC ACT ACA GAA GAC AAT TAT TCA CGT TTA AGG TCA     547
Thr Cys Thr Thr Asn Thr Thr Glu Asp Asn Tyr Ser Arg Leu Arg Ser
        135                 140                 145

TAC CAA GTT TCC CTT CAC TGC ACC TGG CTT GTT GGC ACA GAT GCC CCT     595
Tyr Gln Val Ser Leu His Cys Thr Trp Leu Val Gly Thr Asp Ala Pro
    150                 155                 160

GAG GAC ACG CAG TAT TTT CTC TAC TAT AGG TAT GGC TCT TGG ACT GAA     643
Glu Asp Thr Gln Tyr Phe Leu Tyr Tyr Arg Tyr Gly Ser Trp Thr Glu
165                 170                 175                 180

GAA TGC CAA GAA TAC AGC AAA GAC ACA CTG GGG AGA AAT ATC GCA TGC     691
Glu Cys Gln Glu Tyr Ser Lys Asp Thr Leu Gly Arg Asn Ile Ala Cys
```

-continued

```
                  185             190                195
TGG TTT CCC AGG ACT TTT ATC CTC AGC AAA GGG CGT GAC TGG CTT GCG      739
Trp Phe Pro Arg Thr Phe Ile Leu Ser Lys Gly Arg Asp Trp Leu Ala
            200             205                210

GTG CTT GTT AAC GGC TCC AGC AAG CAC TCT GCT ATC AGG CCC TTT GAT      787
Val Leu Val Asn Gly Ser Ser Lys His Ser Ala Ile Arg Pro Phe Asp
            215             220                225

CAG CTG TTT GCC CTT CAC GCC ATT GAT CAA ATA AAT CCT CCA CTG AAT      835
Gln Leu Phe Ala Leu His Ala Ile Asp Gln Ile Asn Pro Pro Leu Asn
            230             235                240

GTC ACA GCA GAG ATT GAA GGA ACT CGT CTC TCT ATC CAA TGG GAG AAA      883
Val Thr Ala Glu Ile Glu Gly Thr Arg Leu Ser Ile Gln Trp Glu Lys
245             250             255                260

CCA GTG TCT GCT TTT CCA ATC CAT TGC TTT GAT TAT GAA GTA AAA ATA      931
Pro Val Ser Ala Phe Pro Ile His Cys Phe Asp Tyr Glu Val Lys Ile
                265             270                275

CAC AAT ACA AGG AAT GGA TAT TTG CAG ATA GAA AAA TTG ATG ACC AAT      979
His Asn Thr Arg Asn Gly Tyr Leu Gln Ile Glu Lys Leu Met Thr Asn
            280             285                290

GCA TTC ATC TCA ATA ATT GAT GAT CTT TCT AAG TAC GAT GTT CAA GTG     1027
Ala Phe Ile Ser Ile Ile Asp Asp Leu Ser Lys Tyr Asp Val Gln Val
            295             300                305

AGA GCA GCA GTG AGC TCC ATG TGC AGA GAG GCA GGG CTC TGG AGT GAG     1075
Arg Ala Ala Val Ser Ser Met Cys Arg Glu Ala Gly Leu Trp Ser Glu
            310             315                320

TGG AGC CAA CCT ATT TAT GTG GGA AAT GAT GAA CAC AAG CCC TTG AGA     1123
Trp Ser Gln Pro Ile Tyr Val Gly Asn Asp Glu His Lys Pro Leu Arg
325             330             335                340

GAG TGG TTT GTC ATT GTG ATT ATG GCA ACC ATC TGC TTC ATC TTG TTA     1171
Glu Trp Phe Val Ile Val Ile Met Ala Thr Ile Cys Phe Ile Leu Leu
                345             350                355

ATT CTC TCG CTT ATC TGT AAA ATA TGT CAT TTA TGG ATC AAG TTG TTT     1219
Ile Leu Ser Leu Ile Cys Lys Ile Cys His Leu Trp Ile Lys Leu Phe
            360             365                370

CCA CCA ATT CCA GCA CCA AAA AGT AAT ATC AAA GAT CTC TTT GTA ACC     1267
Pro Pro Ile Pro Ala Pro Lys Ser Asn Ile Lys Asp Leu Phe Val Thr
            375             380                385

ACT AAC TAT GAG AAA GCT GGA ATT TAAATTCAAG CATGTTTTAA CTTTTGGTTT    1321
Thr Asn Tyr Glu Lys Ala Gly Ile
390             395

AAGGTACTTG GGTGTACCTG GCAGTGTTGT AAGCTCTTTA CATTAATTAA TTAACTCTCT   1381

AGGTACTGTT ATCTTCATTT TATAAACAAG GCAGCTGAAG TTGAGAGAAA TAAGTAACCT   1441

GTCCTAGGTC ACACAATTAG GAAATGACAG ATCTGGCAGT CTATTTCCAG GCAGTCTATT   1501

TCCACGAGGT CATGAGTGCG AAAGAGGGAC TAGGGGAAGA ATGATTAACT CCAGGGAGCT   1561

GACTTTTCTA GTGTGCTTAC CTGTTTTGCA TCTCTCAAGG ATGTGCCATG AAGCTGTAGC   1621

CAGGTGGAAT TGTACCACAG CCCTGACATG AACACCTGAT GGCAGCTGCT GGGTTGGAGC   1681

CTAGACAAAA ACATGAAGAA CCATGGCTGC TGCCTGAGCC CATCGTGCTG TAATTATAGA   1741

AAACCTTCTA AGGGAAGAAT ATGCTGATAT TTTTCAGATA AGTACCCCTT TTATAAAAAT   1801

CCTCCAAGTT AGCCCTCGAT TTTCCATGTA AGGAAACAGA GGCTTTGAGA TAATGTCTGT   1861

CTCCTAAGGG ACAAAGCCAG GACTTGATCC TGTCTTAAAA ATGCAAAATG TAGTACTTCT   1921

TCCATCAAAG GTAGACATGC ACTAAGGGAC AGGTTTTGGC TTGGTATCAG AATACATTTT   1981

TAAAAGCTGT GTAAGAATTG AACGGGCTGT ACTAGGGGGT ATA                    2024
```